US010167461B2

(12) United States Patent
Schnorr et al.

(10) Patent No.: US 10,167,461 B2
(45) Date of Patent: Jan. 1, 2019

(54) POLYPEPTIDES HAVING CELLULOLYTIC ENHANCING ACTIVITY AND POLYNUCLEOTIDES ENCODING SAME

(71) Applicants: Novozymes, Inc., Davis, CA (US); Novoyzmes A/S, Bagsvaerd (DK)

(72) Inventors: Kirk Schnorr, Holt (DK); Randall Kramer, Lincoln, CA (US)

(73) Assignees: Novozymes, Inc., Davis, CA (US); Novozymes A/S, Bagsvaerd (DK)

( * ) Notice: Subject to any disclaimer, the term of this patent is extended or adjusted under 35 U.S.C. 154(b) by 63 days.

(21) Appl. No.: 15/049,860

(22) Filed: Feb. 22, 2016

(65) Prior Publication Data
US 2016/0168551 A1    Jun. 16, 2016

Related U.S. Application Data

(62) Division of application No. 13/817,754, filed as application No. PCT/US2011/049692 on Aug. 30, 2011, now Pat. No. 9,303,074.

(60) Provisional application No. 61/378,320, filed on Aug. 30, 2010.

(51) Int. Cl.
| | |
|---|---|
| *C12N 9/24* | (2006.01) |
| *C12N 15/82* | (2006.01) |
| *C07K 14/38* | (2006.01) |
| *C12N 9/42* | (2006.01) |
| *C12N 15/62* | (2006.01) |
| *C12P 19/02* | (2006.01) |
| *C12P 19/12* | (2006.01) |
| *C12P 19/14* | (2006.01) |

(52) U.S. Cl.
CPC ............ *C12N 9/2437* (2013.01); *C07K 14/38* (2013.01); *C12N 9/2434* (2013.01); *C12N 15/62* (2013.01); *C12N 15/8246* (2013.01); *C12P 19/02* (2013.01); *C12P 19/12* (2013.01); *C12P 19/14* (2013.01); *C12Y 302/01004* (2013.01)

(58) Field of Classification Search
None
See application file for complete search history.

(56) References Cited

U.S. PATENT DOCUMENTS

| | | | |
|---|---|---|---|
| 5,945,580 | A | 8/1999 | Dunsmuir |
| 6,656,513 | B2 | 12/2003 | Van Beckhoven |
| 7,271,244 | B2 | 9/2007 | Dotson et al. |
| 8,101,393 | B2 | 1/2012 | Gray et al. |
| 8,592,195 | B2 | 11/2013 | Puranen et al. |
| 2006/0095279 | A1 | 5/2006 | Benco et al. |
| 2008/0201805 | A1 | 8/2008 | Krogh et al. |
| 2008/0289066 | A1* | 11/2008 | Lanahan .............. C12N 9/2422 800/298 |
| 2009/0019608 | A1 | 1/2009 | Lopez de Leon et al. |
| 2009/0148901 | A1 | 6/2009 | Lopez de Leon et al. |
| 2011/0111453 | A1 | 5/2011 | McBrayer |

FOREIGN PATENT DOCUMENTS

| | | |
|---|---|---|
| EP | 1479765 A2 | 11/2004 |
| WO | 199700962 A1 | 1/1997 |
| WO | 199700964 A1 | 1/1997 |
| WO | 199906574 A1 | 2/1999 |
| WO | 2004018662 A2 | 3/2004 |
| WO | 2004078919 A2 | 9/2004 |
| WO | 2005074647 A2 | 8/2005 |
| WO | 2005074656 A2 | 8/2005 |
| WO | 2006114095 A1 | 11/2006 |
| WO | 2007109441 A2 | 9/2007 |
| WO | 2008034648 A1 | 3/2008 |
| WO | 2008037757 A1 | 4/2008 |
| WO | 2009042871 A1 | 4/2009 |
| WO | 2009085859 A2 | 7/2009 |
| WO | 2009133034 A1 | 11/2009 |
| WO | 2010022518 A1 | 3/2010 |
| WO | 2010072224 A1 | 7/2010 |
| WO | 2010076387 A1 | 7/2010 |
| WO | 2010088387 A1 | 8/2010 |
| WO | 2010126772 A1 | 11/2010 |
| WO | 2011041405 A1 | 4/2011 |

OTHER PUBLICATIONS

Pel et al, Locus A2QR94 (2007).*
Yu et al, Locus ACF78974 (2008).*
Pel et al, Nature Biotechnology 25(2): 221-231 and Supplemental Table 17 (2007).*
Pel et al. Locus A2QZE1 (2007).*
Brux et al, 2006, J Mol Biol 359(1), 97-109.
Espagne et al, 2008—Uniprot Access No. B2ARI1.
Hamid et al, 2008, Biotechnol Lett 30(12), 2165-2172.
Harris et al, 2010, Biochem 49(15), 3305-3316.
Kanamasa et al, 2003, J Biosci Bioeng 95(6), 627-629.
Koseki et al, 2007, App Microbio and Biotech 77(6), 1279-1285.
Mahajan et al, 2010, Appl Microbiol Biotechnol 86 (6), 1903-1914.
Naika et al, 2007, J Agric Food Chem 55(18), 7566-7572.
Pauly et al, 1999, Glycobiol 9(1), 93-100.
Pel et al, 2007, Nature Biotech 25(2), 221-231.
Pel et al, 2008, NCBI Access No. XM_001396955.
Shallom et al, 2003, Curr Opinion Microbiol 6 (3), 219-228.
Skjoet et al, 2001, Mol Genet Geno 265(5), 913-921.
Takada et al, 1998—Uniprot Acces No. 059843.
Takada et al, 1998, Biosci Biotechnol Biochem 62(8), 1615-1618.

(Continued)

*Primary Examiner* — David T Fox
(74) *Attorney, Agent, or Firm* — Robert Starnes

(57) ABSTRACT

The present invention relates to isolated polypeptides having cellulolytic enhancing activity and isolated polynucleotides encoding the polypeptides. The invention also relates to nucleic acid constructs, vectors, and host cells comprising the polynucleotides as well as methods of producing and using the polypeptides.

22 Claims, 4 Drawing Sheets

Specification includes a Sequence Listing.

(56) References Cited

OTHER PUBLICATIONS

Takada et al, 2002, J Biosci Bioeng 94(5), 482-485.
Vuong et al, 2010, Biotech and Bioengi 107(2), 195-205.
Ito et al, 2007, J Mol Catalys 49(1-4), 92-97.
Brenner et al, 1999, Trends in Genetic 14(6), 248-25.
Broun et al, 1998, Science 282, 1315-1317.
Doerks et al, 1998, TIG 14(6), 248-250.
Emanuelsson, 2007, Nat Protoc 2(4), 953-971.
Fourgoux et al, 1999, Plant Mol Biol 40, 857-872.
Jordan et al, 2010, Appl Microbiol Biotechnol 86, 1647-1658.
Lee et al, 2011, Protein Sci 20, 1935-1940.
Leggio et al2002, FEBS Lett 523, 103-108.
Momeni et al, 2013, J Biol Chem 288 (8), 5861-5872.
Maniatis et al, 1982, A Laboratory Manual 324-343, 387-389.
Ngo et al, 1994, Prot Fold Prob Tertiary Struc Predic 492-495.
Petegem, 2002, Biochem Biophys Res Com 296, 161-166.
Van De Loo et al, 1995, PNAS 92, 6743-6747.
Moroz et al, 2015, Acta Crystall Sec F, F71, 114-120.
Takada et al, 1998, J Ferment Bioeng 85(1), 1-9.
Rashid et al, 2008, Biotechnol Lett 30(12), 2165-2172.
Murao et al., 1979, J. Ferm Technol 57 (3), 151-156.
Gawande et al, 1999, J Appl Microbiol 87, 511-519.
Anonymous, UniProt Access A2R5J7, 2010.
Suo et al, 2004, PNAS 101(25), 9205-9210.
Anonymous, UniProt A1DMR8.
Pozzo et al, 2010, J. Mol Biol 397, 724-739.
Pel et al, 2007—Uniport Access No. A2QBA9.
Pel et al, 2007—Uniport Access No. A2R5J9.

* cited by examiner

SEQUENCE LISTING

<160> NUMBER OF SEQ ID NOS: 28

<210> SEQ ID NO 1
<211> LENGTH: 1035
<212> TYPE: DNA
<213> ORGANISM: Aspergillus aculeatus

<400> SEQUENCE: 1

```
atgaagtata ttcctctcgt tattgcagtt gctgccggcc tggcacgtcc ggctactgcc      60
cactacatct tcagcaagct cgtgctgaac ggagaggcat ctgcggactg gcaatacatc     120
cgcgagacta ctcgcagcat agtctatgag ccgaccaagt acacctctac cttcgataac     180
ctaacaccca gcgatagcga cttccgctgt aatctcggtt ccttcagcaa tgctgcgaag     240
accgaggtcg ctgaggttgc ggcaggcgat accatcgcaa tgaagctatt ctacgacacc     300
agtattgcgc atcctggccc gggacaagtt tatatgtcca aggcaccgac cggcaatgtt     360
caggaatacc aaggagacgg ggattggttc aaaatctggg aaaagaccct ttgcaacacg     420
gatggtgatc tgactacaga ggcctggtgc acctggggca tgtcacagtt tgaatttcaa     480
atcccagctg cgaccccggc aggagagtac ctagtgcgcg ccgagcatat aggcctgcat     540
ggcgctcaag cgaacgaggc cgaattcttc tacagctgtg cgcagatcaa ggttacaggc     600
tcgggaactg gatctcccag tctcacgtat caaattcctg gtctctataa cgacactatg     660
accctgttca atggcctcaa tctttggact gattcagccg agaaggtgca gctggatttc     720
ctggagacgc caattgggga cgacgtgtgg agcggagcag gctcggggag cccatctgct     780
gccacctctt cgaccagcgg tgcaactctt gcagctcagg tacaactac ctctgccgcg     840
catgctcagg cccagaccac cattaccacc agcaccagca ccatcacgtc tctcgaatca     900
gccagctcaa ccgatctcgt tgcgcagtat ggtcagtgcg gaggccttaa ctggtccggt     960
ccaaccgagt gtgagacacc ttatacctgt gtgcagcaga accttactac ccatcaatgc    1020
gtgaattcgt gctga                                                    1035
```

<210> SEQ ID NO 2
<211> LENGTH: 344
<212> TYPE: PRT
<213> ORGANISM: Aspergillus aculeatus

<400> SEQUENCE: 2

```
Met Lys Tyr Ile Pro Leu Val Ile Ala Val Ala Ala Gly Leu Ala Arg
1               5                   10                  15

Pro Ala Thr Ala His Tyr Ile Phe Ser Lys Leu Val Leu Asn Gly Glu
            20                  25                  30

Ala Ser Ala Asp Trp Gln Tyr Ile Arg Glu Thr Thr Arg Ser Ile Val
        35                  40                  45

Tyr Glu Pro Thr Lys Tyr Thr Ser Thr Phe Asp Asn Leu Thr Pro Ser
    50                  55                  60

Asp Ser Asp Phe Arg Cys Asn Leu Gly Ser Phe Ser Asn Ala Ala Lys
65                  70                  75                  80

Thr Glu Val Ala Glu Val Ala Ala Gly Asp Thr Ile Ala Met Lys Leu
                85                  90                  95

Phe Tyr Asp Thr Ser Ile Ala His Pro Gly Pro Gly Gln Val Tyr Met
            100                 105                 110

Ser Lys Ala Pro Thr Gly Asn Val Gln Glu Tyr Gln Gly Asp Gly Asp
        115                 120                 125

Trp Phe Lys Ile Trp Glu Lys Thr Leu Cys Asn Thr Asp Gly Asp Leu
```

```
                 130               135                140
Thr Thr Glu Ala Trp Cys Thr Trp Gly Met Ser Gln Phe Glu Phe Gln
145                 150                 155                 160

Ile Pro Ala Ala Thr Pro Ala Gly Glu Tyr Leu Val Arg Ala Glu His
                165                 170                 175

Ile Gly Leu His Gly Ala Gln Ala Asn Glu Ala Glu Phe Phe Tyr Ser
            180                 185                 190

Cys Ala Gln Ile Lys Val Thr Gly Ser Gly Thr Gly Ser Pro Ser Leu
        195                 200                 205

Thr Tyr Gln Ile Pro Gly Leu Tyr Asn Asp Thr Met Thr Leu Phe Asn
    210                 215                 220

Gly Leu Asn Leu Trp Thr Asp Ser Ala Glu Lys Val Gln Leu Asp Phe
225                 230                 235                 240

Leu Glu Thr Pro Ile Gly Asp Asp Val Trp Ser Gly Ala Gly Ser Gly
                245                 250                 255

Ser Pro Ser Ala Ala Thr Ser Ser Thr Ser Gly Ala Thr Leu Ala Ala
                260                 265                 270

Gln Gly Thr Thr Thr Ser Ala Ala His Ala Gln Ala Gln Thr Thr Ile
            275                 280                 285

Thr Thr Ser Thr Ser Thr Ile Thr Ser Leu Glu Ser Ala Ser Ser Thr
    290                 295                 300

Asp Leu Val Ala Gln Tyr Gly Gln Cys Gly Gly Leu Asn Trp Ser Gly
305                 310                 315                 320

Pro Thr Glu Cys Glu Thr Pro Tyr Thr Cys Val Gln Gln Asn Pro Tyr
                325                 330                 335

Tyr His Gln Cys Val Asn Ser Cys
            340

<210> SEQ ID NO 3
<211> LENGTH: 1203
<212> TYPE: DNA
<213> ORGANISM: Aspergillus aculeatus

<400> SEQUENCE: 3
atgtctgttg ctaagtttgc tggtgttatc ctcggttcgg ccgctctcgt cgctggccac      60
ggttacgtgt cgggtgctgt tgtcgacgga acctactatg cggctacat tgtcacttcc      120 taccctat  ccagcgatcc cccggagacc attggatggt ctaccgaggc gaccgacttg      180 ggttcgtcg atggtagcga gtatgctgat gccgacatca tttgccacaa gagtgccaag      240
cccggtgcca tctctgctga ggtcaaggcc ggtggtactg ttgagctcca gtggactacc      300
tggcccgaca gccaccacgg ccctgtcctg acctaccttg ccaactgcaa tggtgactgc      360
agcagcgtca ccaagaccga cctcgagttt ttcaagattg acgagagcgg tctcatcaac      420
gacgacgacg tccccggtac ctgggccagt gataacttga tcgccaacaa caacagctgg      480
actgtgacca tcccctctga cattgcggct ggcaactacg tcctccgtca cgaaatcatt      540
gcccttcact ctgctggtaa caaggatggt gctcagaact accctcagtg cctcaacttg      600
aaggtcactg gcggcggtga tctcgctcct tctggcactg ctggtgagag cctgtacaag      660
gacaccgatg ctggtatcct cgtcaacatc taccagtctc tttcctccta cgatattccc      720
ggacctgcta tgtacaacgc tacctccagc cctccagct cctccagctc cagctccagc      780
tccagctcca gctccagctc cggctcttcc agctccgccg ccgcctccag cagctccagc      840
agctccagca ctactgccgc cgccgccgcc gctaccagcg ctgcttcttc cgtcacctct      900
```

```
gctgctggct ccgtcgttac tcagactgct accgctgttg agactgatac tgccactgcc    960
taccagacct ccactgaggt tgcgcaagtc accgtcaccg gtagcgctcc ccagcagacc   1020
tacgttgcca ctcccagcag ctccagctct gcctccagca gctccagtgc ttccgtatcc   1080
accagcacca gcctccaccag ctacttcgag tccctgagcg ctgatcagtt cctcagcgtt   1140
ctcaagcaga ctttcacctg gttggtcagc gagaagaagc acgcccgtga cctctccgcc   1200
taa                                                                 1203
```

<210> SEQ ID NO 4
<211> LENGTH: 400
<212> TYPE: PRT
<213> ORGANISM: Aspergillus aculeatus

<400> SEQUENCE: 4

```
Met Ser Val Ala Lys Phe Ala Gly Val Ile Leu Gly Ser Ala Ala Leu
1               5                   10                  15

Val Ala Gly His Gly Tyr Val Ser Gly Ala Val Asp Gly Thr Tyr Tyr
            20                  25                  30

Tyr Gly Gly Tyr Ile Val Thr Ser Tyr Pro Tyr Ser Ser Asp Pro Pro
        35                  40                  45

Glu Thr Ile Gly Trp Ser Thr Glu Ala Thr Asp Leu Gly Phe Val Asp
    50                  55                  60

Gly Ser Glu Tyr Ala Asp Ala Asp Ile Ile Cys His Lys Ser Ala Lys
65                  70                  75                  80

Pro Gly Ala Ile Ser Ala Glu Val Lys Ala Gly Gly Thr Val Glu Leu
                85                  90                  95

Gln Trp Thr Thr Trp Pro Asp Ser His His Gly Pro Val Leu Thr Tyr
            100                 105                 110

Leu Ala Asn Cys Asn Gly Asp Cys Ser Ser Val Thr Lys Thr Asp Leu
        115                 120                 125

Glu Phe Phe Lys Ile Asp Glu Ser Gly Leu Ile Asn Asp Asp Asp Val
    130                 135                 140

Pro Gly Thr Trp Ala Ser Asp Asn Leu Ile Ala Asn Asn Ser Trp
145                 150                 155                 160

Thr Val Thr Ile Pro Ser Asp Ile Ala Ala Gly Asn Tyr Val Leu Arg
                165                 170                 175

His Glu Ile Ile Ala Leu His Ser Ala Gly Asn Lys Asp Gly Ala Gln
            180                 185                 190

Asn Tyr Pro Gln Cys Leu Asn Leu Lys Val Thr Gly Gly Asp Leu
        195                 200                 205

Ala Pro Ser Gly Thr Ala Gly Glu Ser Leu Tyr Lys Asp Thr Asp Ala
    210                 215                 220

Gly Ile Leu Val Asn Ile Tyr Gln Ser Leu Ser Ser Tyr Asp Ile Pro
225                 230                 235                 240

Gly Pro Ala Met Tyr Asn Ala Thr Ser Ser Ser Ser Ser Ser Ser
                245                 250                 255

Ser Ser Ser Ser Ser Ser Ser Ser Ser Gly Ser Ser Ser
            260                 265                 270

Ala Ala Ala Ser Ser Ser Ser Ser Ser Thr Thr Ala Ala
        275                 280                 285

Ala Ala Ala Thr Ser Ala Ala Ser Ser Val Thr Ser Ala Ala Gly Ser
    290                 295                 300

Val Val Thr Gln Thr Ala Thr Ala Val Glu Thr Asp Thr Ala Thr Ala
305                 310                 315                 320
```

Tyr Gln Thr Ser Thr Glu Val Ala Gln Val Thr Val Thr Gly Ser Ala
            325                 330                 335

Pro Gln Gln Thr Tyr Val Ala Thr Pro Ser Ser Ser Ser Ala Ser
        340                 345                 350

Ser Ser Ser Ser Ala Ser Val Ser Thr Ser Thr Ser Leu Thr Ser Tyr
        355                 360                 365

Phe Glu Ser Leu Ser Ala Asp Gln Phe Leu Ser Val Leu Lys Gln Thr
        370                 375                 380

Phe Thr Trp Leu Val Ser Glu Lys Lys His Ala Arg Asp Leu Ser Ala
385                 390                 395                 400

<210> SEQ ID NO 5
<211> LENGTH: 1170
<212> TYPE: DNA
<213> ORGANISM: Aspergillus aculeatus

<400> SEQUENCE: 5

```
atgaagtcct ctactttcgg tatgctcgct ctggcagcag cagccaagat ggtcgatgcc      60
cacaccaccg tcttcgccgt ctggatcaac ggcgaggacc agggtctggg caacagtgcc     120
agtggctaca tccggtctcc ccccagcaac agccccgtca aggacgtgac ctcgaccgac     180
atcacctgca acgtcaacgg cgaccaggcg gcggctaaga ccctctccgt caagggcggc     240
gacgtcgtca ccttcgagtg gcaccacgac agccgggacc cctccgacga catcatcgcc     300
tcctcccaca agggccccgt catggtctac atggccccga ccaccgccgg cagcagcggc     360
aagaactggg tcaagatcgc cgaggacgga tactccgacg gcacctgggc cgtcgacacc     420
ctgatcgcca cagcggcaa gcacaacatc accgtccccg acgtccccgc cggcgactac     480
ctcttccgcc cggagatcat cgccctccac gaggccgaga cgagggcgg cgcccagttc     540
tacatggagt gtgtccagtt caaggtcacc tccgacggtg ccaacactct gcccgacggt     600
gtcagcctgc ccggcgccta ctccgccact gaccccggta tcctcttcaa catgtacggc     660
tccttcgaca gctatcccat ccccggtccc tccgtctggg atggcactag ctctggctct     720
tcctcttctt cctcttcttc ctcttccagc tcttccgccg ccgctgccgt tgttgccacc     780
tcctcttcct cttcctctgc ttccatcgag gccgtgacca ccaagggtgc cgtcgccgcc     840
gtctccaccg ccgccgccgt ggctcctacc accaccaccg ctgccccac caccttcgcc     900
acggccgtcg cctccaccaa gaaggccact gcctgccgca caagaccaa gtcctcctcc     960
gctgccacca ccgccgccgc cgtcgccgag accacctctt ccaccgctgc cgccaccgct    1020
gctgcttcct ctgcctcttc cgcctccggc accgccggca agtacgagcg ctgcggtggc    1080
cagggctgga ccggtgccac cacctgcgtt gatggctgga cctgcaagca gtggaaccct    1140
tactactacc agtgcgttga gtctgcctag                                    1170
```

<210> SEQ ID NO 6
<211> LENGTH: 389
<212> TYPE: PRT
<213> ORGANISM: Aspergillus aculeatus

<400> SEQUENCE: 6

Met Lys Ser Ser Thr Phe Gly Met Leu Ala Leu Ala Ala Ala Ala Lys
1               5                   10                  15

Met Val Asp Ala His Thr Thr Val Phe Ala Val Trp Ile Asn Gly Glu
            20                  25                  30

Asp Gln Gly Leu Gly Asn Ser Ala Ser Gly Tyr Ile Arg Ser Pro Pro

```
                  35                  40                  45
Ser Asn Ser Pro Val Lys Asp Val Thr Ser Thr Asp Ile Thr Cys Asn
             50                  55                  60

Val Asn Gly Asp Gln Ala Ala Lys Thr Leu Ser Val Lys Gly Gly
 65                  70                  75                  80

Asp Val Val Thr Phe Glu Trp His His Asp Ser Arg Asp Ala Ser Asp
                     85                  90                  95

Asp Ile Ile Ala Ser Ser His Lys Gly Pro Val Met Val Tyr Met Ala
                100                 105                 110

Pro Thr Thr Ala Gly Ser Ser Gly Lys Asn Trp Val Lys Ile Ala Glu
                115                 120                 125

Asp Gly Tyr Ser Asp Gly Thr Trp Ala Val Asp Thr Leu Ile Ala Asn
                130                 135                 140

Ser Gly Lys His Asn Ile Thr Val Pro Asp Val Pro Ala Gly Asp Tyr
145                 150                 155                 160

Leu Phe Arg Pro Glu Ile Ile Ala Leu His Glu Ala Glu Asn Glu Gly
                165                 170                 175

Gly Ala Gln Phe Tyr Met Glu Cys Val Gln Phe Lys Val Thr Ser Asp
                180                 185                 190

Gly Ala Asn Thr Leu Pro Asp Gly Val Ser Leu Pro Gly Ala Tyr Ser
                195                 200                 205

Ala Thr Asp Pro Gly Ile Leu Phe Asn Met Tyr Gly Ser Phe Asp Ser
210                 215                 220

Tyr Pro Ile Pro Gly Pro Ser Val Trp Asp Gly Thr Ser Ser Gly Ser
225                 230                 235                 240

Ser Ser Ser Ser Ser Ser Ser Ser Ser Ser Ala Ala Ala
                245                 250                 255

Val Val Ala Thr Ser Ser Ser Ser Ala Ser Ile Glu Ala Val
                260                 265                 270

Thr Thr Lys Gly Ala Val Ala Ala Val Ser Thr Ala Ala Ala Val Ala
                275                 280                 285

Pro Thr Thr Thr Thr Ala Ala Pro Thr Thr Phe Ala Thr Ala Val Ala
                290                 295                 300

Ser Thr Lys Lys Ala Thr Ala Cys Arg Asn Lys Thr Lys Ser Ser Ser
305                 310                 315                 320

Ala Ala Thr Thr Ala Ala Ala Val Ala Glu Thr Thr Ser Ser Thr Ala
                325                 330                 335

Ala Ala Thr Ala Ala Ala Ser Ser Ala Ser Ser Ala Ser Gly Thr Ala
                340                 345                 350

Gly Lys Tyr Glu Arg Cys Gly Gly Gln Gly Trp Thr Gly Ala Thr Thr
                355                 360                 365

Cys Val Asp Gly Trp Thr Cys Lys Gln Trp Asn Pro Tyr Tyr Tyr Gln
                370                 375                 380

Cys Val Glu Ser Ala
385

<210> SEQ ID NO 7
<211> LENGTH: 1221
<212> TYPE: DNA
<213> ORGANISM: Aspergillus aculeatus

<400> SEQUENCE: 7
atgcgtcagg ctcagtcttt gtccctcttg acagctcttc tgtctgccac gcgtgtggct      60
ggacacggtc acgtcactaa cgttgtcgtc aacggtgttt actacgaggg cttcgatatc     120
```

```
aacagcttcc cctacgagtc cgatccccct aaggtggcgg cttggaccac tcctaacact    180
ggcaacggtt tcatttcccc cagcgactac ggtaccgatg acattatttg ccaccagaat    240
gccaccaacg cccaggccca cattgttgtt gcggctggtg acaagatcaa catccagtgg    300
accgcgtggc ccgattccca ccacggtcct gtccttgact acctcgctcg ctgcgacggt    360
gagtgtgaga cggttgataa gaccactctt gagtttttca agatcgacgg cgtcggtctc    420
atcagtgaca ccgaagtgcc cggtacctgg ggagatgacc agctgatcgc caacaacaac    480
agctggttgg tcgagatccc cccgaccatt gctcctggca actatgttct cgccacgag    540 cttatcgctc tccacagcgc cggcactgaa gatggtgctc agaactaccc ccagtgtttc    600
aacctccagg tcactggctc cggtactgac gagcccgctg gtaccctcgg caccaagctc    660
tacactgagg atgaggctgg tatcgttgtg aacatctaca cctctctgtc ttcctatgcc    720
gtccccggcc ccacccagta cagcggcgcc gtctctgtca gccaatccac ttcggccatt    780
acctccaccg gaactgctgt tgtcggtagc ggcagcgctg ttgccacctc tgccgccgcg    840
gctaccacca gcgctgctgc ttcttctgcc gctgctgcta ccaccgctgc tgccgttacc    900
agcgccaatg ccaacactca gattgcccag cccagcagca gctcttctta ctcccagatc    960
gccgtgcagg tgcctcctc ctggaccacc cttgtgaccg tcactcctcc cgccgccgcc   1020
gccaccaccc ctgctgccgt ccctgagcct cagacccct ctgccagctc tggagccacc   1080
actaccagca gcagcagcgg cgccgcccag tctctctacg ccagtgcgg tggtatcaac   1140 tggaccggag ctacctcttg cgttgagggc gctacttgct accagtacaa cccttactac   1200
taccagtgca tctctgccta a                                             1221

<210> SEQ ID NO 8
<211> LENGTH: 406
<212> TYPE: PRT
<213> ORGANISM: Aspergillus aculeatus

<400> SEQUENCE: 8

Met Arg Gln Ala Gln Ser Leu Ser Leu Leu Thr Ala Leu Leu Ser Ala
1               5                   10                  15

Thr Arg Val Ala Gly His Gly His Val Thr Asn Val Val Asn Gly
            20                  25                  30

Val Tyr Tyr Glu Gly Phe Asp Ile Asn Ser Phe Pro Tyr Glu Ser Asp
        35                  40                  45

Pro Pro Lys Val Ala Ala Trp Thr Thr Pro Asn Thr Gly Asn Gly Phe
    50                  55                  60

Ile Ser Pro Ser Asp Tyr Gly Thr Asp Ile Ile Cys His Gln Asn
65                  70                  75                  80

Ala Thr Asn Ala Gln Ala His Ile Val Val Ala Gly Asp Lys Ile
                85                  90                  95

Asn Ile Gln Trp Thr Ala Trp Pro Asp Ser His His Gly Pro Val Leu
            100                 105                 110

Asp Tyr Leu Ala Arg Cys Asp Gly Glu Cys Glu Thr Val Asp Lys Thr
        115                 120                 125

Thr Leu Glu Phe Phe Lys Ile Asp Gly Val Gly Leu Ile Ser Asp Thr
    130                 135                 140

Glu Val Pro Gly Thr Trp Gly Asp Asp Gln Leu Ile Ala Asn Asn Asn
145                 150                 155                 160

Ser Trp Leu Val Glu Ile Pro Pro Thr Ile Ala Pro Gly Asn Tyr Val
                165                 170                 175
```

Leu Arg His Glu Leu Ile Ala Leu His Ser Ala Gly Thr Glu Asp Gly
            180                 185                 190

Ala Gln Asn Tyr Pro Gln Cys Phe Asn Leu Gln Val Thr Gly Ser Gly
            195                 200                 205

Thr Asp Glu Pro Ala Gly Thr Leu Gly Thr Lys Leu Tyr Thr Glu Asp
    210                 215                 220

Glu Ala Gly Ile Val Val Asn Ile Tyr Thr Ser Leu Ser Ser Tyr Ala
225                 230                 235                 240

Val Pro Gly Pro Thr Gln Tyr Ser Gly Ala Val Ser Val Ser Gln Ser
                245                 250                 255

Thr Ser Ala Ile Thr Ser Thr Gly Thr Ala Val Val Gly Ser Gly Ser
            260                 265                 270

Ala Val Ala Thr Ser Ala Ala Ala Thr Thr Ser Ala Ala Ala Ser
            275                 280                 285

Ser Ala Ala Ala Ala Thr Thr Ala Ala Ala Val Thr Ser Ala Asn Ala
    290                 295                 300

Asn Thr Gln Ile Ala Gln Pro Ser Ser Ser Ser Tyr Ser Gln Ile
305                 310                 315                 320

Ala Val Gln Val Pro Ser Ser Trp Thr Thr Leu Val Thr Val Thr Pro
                325                 330                 335

Pro Ala Ala Ala Thr Thr Pro Ala Ala Val Pro Glu Pro Gln Thr
            340                 345                 350

Pro Ser Ala Ser Ser Gly Ala Thr Thr Thr Ser Ser Ser Gly Ala
    355                 360                 365

Ala Gln Ser Leu Tyr Gly Gln Cys Gly Gly Ile Asn Trp Thr Gly Ala
    370                 375                 380

Thr Ser Cys Val Glu Gly Ala Thr Cys Tyr Gln Tyr Asn Pro Tyr Tyr
385                 390                 395                 400

Tyr Gln Cys Ile Ser Ala
            405

<210> SEQ ID NO 9
<211> LENGTH: 1284
<212> TYPE: DNA
<213> ORGANISM: Aspergillus aculeatus

<400> SEQUENCE: 9
atgtctcttt ccaagattgc cactcttctg ctgggctcgg tctcgctggt cgctggtcat    60
gggtatgtct cgagcatcga ggtggacggt accacctatg agggtacttt ggtcgacact   120
tattactacg aatccgaccc gcccgagtta atcgcctggt ccacaaatgc cacgatgat    180 ggctatgtat cgcccctccga ctacgagagc gtgaacatca tctgccacaa ggggtctgcg   240
cccggcgcgt tgtcggcccc tgtcgcgccc ggaggctggg tgcagatgac ctggaacacc   300
tggcccaccg accatcacgg ccctgtcatc acgtatatgg ccaattgcca cggttcttgc   360
gcagatgtgg acaagaccac cctcgagttc ttcaagatcg atgctggcgg cttgatcgat   420
gacacggacg tgcctggaac ttgggcgacc gatgagctca ttgaagatag ctatagtcgc   480
aacatcacta tccccagcga tattgccccc gggtactatg ttttgcgaca cgagatcatt   540
gctctgcaca cgcgccagaa cctggacgga gcccagaact accccagtg catcaatctg   600 gaagtcaccg gcagcgagac agcaaccccg agtggcacct gggcactgc tctgtacaag   660 gagaccgacc ccggcatcta tgttgacatc tggaacacgt tgagcacgta ctattccc     720 ggccccgcgc tgtacactgc tggtagcact gcgaccgcag ccgctgctgc cgataccacc   780

```
actacttctg ctggcaccac cgctgaggcc accaccgctg ccgccgccgt gagtaccacc    840
gcggacgctg ttccgaccga gtcttcagct ccttccgaga ccagcgcgac taccgcgaac    900
cctgctcggc ccactgccgg cagcgacatc cgcttccagc ccggtcaggt caaggctggt    960
gcttcagtca caactcggc tactgagact tcctctggtg agtctgccac gacgaccaca   1020
acatcagtgg ccactgcggc ttcgagcgcg gattcgtcga cgacttctgg ggttttgagt   1080
ggcgcctgca gccaggaggg ctactggtac tgcaacgggg gcactgcgtt ccagcgctgt   1140
gtcaacgggg aatgggatgc gtcccagagt gtggctgcgg gcacggtctg caccgccggt   1200
atctcggaga ccatcaccat ttcagccgcc gccacgcgcc gggatgccat gcgtcgtcat   1260
ctggcgcgtc ccaagcgtca ctga                                          1284
```

<210> SEQ ID NO 10
<211> LENGTH: 427
<212> TYPE: PRT
<213> ORGANISM: Aspergillus aculeatus

<400> SEQUENCE: 10

```
Met Ser Leu Ser Lys Ile Ala Thr Leu Leu Gly Ser Val Ser Leu
1               5                   10                  15

Val Ala Gly His Gly Tyr Val Ser Ser Ile Glu Val Asp Gly Thr Thr
                20                  25                  30

Tyr Gly Gly Tyr Leu Val Asp Thr Tyr Tyr Glu Ser Asp Pro Pro
        35                  40                  45

Glu Leu Ile Ala Trp Ser Thr Asn Ala Thr Asp Asp Gly Tyr Val Ser
50                  55                  60

Pro Ser Asp Tyr Glu Ser Val Asn Ile Ile Cys His Lys Gly Ser Ala
65                  70                  75                  80

Pro Gly Ala Leu Ser Ala Pro Val Ala Pro Gly Gly Trp Val Gln Met
                85                  90                  95

Thr Trp Asn Thr Trp Pro Thr Asp His His Gly Pro Val Ile Thr Tyr
                100                 105                 110

Met Ala Asn Cys His Gly Ser Cys Ala Asp Val Asp Lys Thr Thr Leu
            115                 120                 125

Glu Phe Phe Lys Ile Asp Ala Gly Gly Leu Ile Asp Asp Thr Asp Val
130                 135                 140

Pro Gly Thr Trp Ala Thr Asp Glu Leu Ile Glu Asp Ser Tyr Ser Arg
145                 150                 155                 160

Asn Ile Thr Ile Pro Ser Asp Ile Ala Pro Gly Tyr Tyr Val Leu Arg
                165                 170                 175

His Glu Ile Ile Ala Leu His Ser Ala Glu Asn Leu Asp Gly Ala Gln
                180                 185                 190

Asn Tyr Pro Gln Cys Ile Asn Leu Glu Val Thr Gly Ser Glu Thr Ala
        195                 200                 205

Thr Pro Ser Gly Thr Leu Gly Thr Ala Leu Tyr Lys Glu Thr Asp Pro
    210                 215                 220

Gly Ile Tyr Val Asp Ile Trp Asn Thr Leu Ser Thr Tyr Thr Ile Pro
225                 230                 235                 240

Gly Pro Ala Leu Tyr Thr Ala Gly Ser Thr Ala Thr Ala Ala Ala
                245                 250                 255

Ala Asp Thr Thr Thr Thr Ser Ala Gly Thr Ala Glu Ala Thr
        260                 265                 270

Ala Ala Ala Ala Val Ser Thr Thr Ala Asp Ala Val Pro Thr Glu Ser
```

```
              275                 280                 285
Ser Ala Pro Ser Glu Thr Ser Ala Thr Thr Ala Asn Pro Ala Arg Pro
    290                 295                 300

Thr Ala Gly Ser Asp Ile Arg Phe Gln Pro Gly Gln Val Lys Ala Gly
305                 310                 315                 320

Ala Ser Val Asn Asn Ser Ala Thr Glu Thr Ser Ser Gly Glu Ser Ala
                325                 330                 335

Thr Thr Thr Thr Thr Ser Val Ala Thr Ala Ser Ser Ala Asp Ser
            340                 345                 350

Ser Thr Thr Ser Gly Val Leu Ser Gly Ala Cys Ser Gln Glu Gly Tyr
        355                 360                 365

Trp Tyr Cys Asn Gly Gly Thr Ala Phe Gln Arg Cys Val Asn Gly Glu
    370                 375                 380

Trp Asp Ala Ser Gln Ser Val Ala Ala Gly Thr Val Cys Thr Ala Gly
385                 390                 395                 400

Ile Ser Glu Thr Ile Thr Ile Ser Ala Ala Ala Thr Arg Arg Asp Ala
                405                 410                 415

Met Arg Arg His Leu Ala Arg Pro Lys Arg His
            420                 425

<210> SEQ ID NO 11
<211> LENGTH: 804
<212> TYPE: DNA
<213> ORGANISM: Aspergillus aculeatus

<400> SEQUENCE: 11
atgcttgtca aactcatctc ttttctttca gctgctacca gcgtagctgc tcatggtcat      60
gtgtcaaaca ttgtgatcaa cggggtgtcc taccgcggat gggacatcaa ttcggaccct     120
tacaattcca accctccggt ggtggttgca tggcaaacac ccaacacagc taatggcttc     180
atctcccctg atgcatacga cacagatgat gttatttgcc atctgagcgc tacgaatgcc     240
agaggccacg cagtcgtcgc tgctggcgac aagatcagcc tccagtggac gacctggcct     300
gacagtcacc atggccctgt catcagctac ctagccaact gcggctccag ctgcgagaca     360
gtcgataaga ccaccctcga gttcttcaag atcgatggtg ttggcttggt ggatgagagc     420
aatccccctg gtatctgggg agacgatgag ctcattgcca acaacaactc ttggctggta     480
gagattccag ctagtatcgc gccaggatac tatgtgctgc gtcacgagtt gatcgctctg     540
catggagcag ggagtgagaa tggagcccag aattacatgc aatgtttcaa ccttcaggtt     600
actgggactg gcacggtcca gccttccggg gtcctgggca cggagctgta caaacccaca     660
gacgctggaa ttcttgtcaa tatctaccag tcgctctcca cctatgttgt tcctggcccg     720
accctgatcc cccaggccgt ttccctcgtt cagtcgagct ccaccattac cgcctcgggc     780
acggcagtga caaccacggc ttga                                             804

<210> SEQ ID NO 12
<211> LENGTH: 267
<212> TYPE: PRT
<213> ORGANISM: Aspergillus aculeatus

<400> SEQUENCE: 12

Met Leu Val Lys Leu Ile Ser Phe Leu Ser Ala Ala Thr Ser Val Ala
1               5                   10                  15

Ala His Gly His Val Ser Asn Ile Val Ile Asn Gly Val Ser Tyr Arg
            20                  25                  30
```

```
Gly Trp Asp Ile Asn Ser Asp Pro Tyr Asn Ser Asn Pro Val Val
         35                  40                  45

Val Ala Trp Gln Thr Pro Asn Thr Ala Asn Gly Phe Ile Ser Pro Asp
 50                  55                  60

Ala Tyr Asp Thr Asp Val Ile Cys His Leu Ser Ala Thr Asn Ala
 65                  70                  75                  80

Arg Gly His Ala Val Ala Ala Gly Asp Lys Ile Ser Leu Gln Trp
                 85                  90                  95

Thr Thr Trp Pro Asp Ser His His Gly Pro Val Ile Ser Tyr Leu Ala
            100                 105                 110

Asn Cys Gly Ser Ser Cys Glu Thr Val Asp Lys Thr Thr Leu Glu Phe
            115                 120                 125

Phe Lys Ile Asp Gly Val Gly Leu Val Asp Ser Asn Pro Pro Gly
            130                 135                 140

Ile Trp Gly Asp Asp Glu Leu Ile Ala Asn Asn Asn Ser Trp Leu Val
145                 150                 155                 160

Glu Ile Pro Ala Ser Ile Ala Pro Gly Tyr Tyr Val Leu Arg His Glu
                165                 170                 175

Leu Ile Ala Leu His Gly Ala Gly Ser Glu Asn Gly Ala Gln Asn Tyr
                180                 185                 190

Met Gln Cys Phe Asn Leu Gln Val Thr Gly Thr Gly Thr Val Gln Pro
                195                 200                 205

Ser Gly Val Leu Gly Thr Glu Leu Tyr Lys Pro Thr Asp Ala Gly Ile
            210                 215                 220

Leu Val Asn Ile Tyr Gln Ser Leu Ser Thr Tyr Val Val Pro Gly Pro
225                 230                 235                 240

Thr Leu Ile Pro Gln Ala Val Ser Leu Val Gln Ser Ser Ser Thr Ile
                245                 250                 255

Thr Ala Ser Gly Thr Ala Val Thr Thr Thr Ala
                260                 265

<210> SEQ ID NO 13
<211> LENGTH: 822
<212> TYPE: DNA
<213> ORGANISM: Aspergillus aculeatus

<400> SEQUENCE: 13
atgaagtatc ttgcgatctt cgcggcagca gcagctggac tggcccgccc gacagcagcg    60
cactacatct tcagcaagct gattctggac ggcgaagtct ctgaggactg cagtatatt   120 cgtaaaacca cccgggagac atgctatttg ccgaccaagt tcaccgacac cttcgacaac   180
ttgactccga cgaccagga tttccggtgc aatctcggct cgttcagcaa cgccgccaag   240
accgaagtgg ccgaggtgga agcgggctcc acgattggca tgcagctttt cgctggtagc   300
cacatgcgtc acccgggacc tgcgcaagtc ttcatgtcta aggccccgtc cggcaacgta   360
cagagctacg agggtgacgg ctcctggttc aagatctggg agcgtacact ctgcgacaaa   420
agtggcgatc tgactggaga tgcgtggtgt acatacggcc agaccgagat cgagtttcaa   480
atccccgagg cgaccccgac gggcgaatac ctggtccgag cggagcacat cggtcttcac   540
cgcgcacaga gtaatcaagc cgagttctac tacagctgcg cccaggtcaa ggtcacgggc   600
aatggtaccg gggtgccgag ccagacatat cagatccctg gcatgtacaa tgaccgctcg   660
gagcttttca cgggctgaa cttgtggtcc tactcggtgg agaacgtcga ggcagccatg   720
aagaattcta tcgtgggtga tgaaatttgg aatggaagtt ctgttccctc tgagtccat    780
```
gtcccgaagt ataagaagag tcatgcttgt cgtgtttatt ga                                                822

<210> SEQ ID NO 14
<211> LENGTH: 273
<212> TYPE: PRT
<213> ORGANISM: Aspergillus aculeatus

<400> SEQUENCE: 14

Met Lys Tyr Leu Ala Ile Phe Ala Ala Ala Ala Gly Leu Ala Arg
1               5                   10                  15

Pro Thr Ala Ala His Tyr Ile Phe Ser Lys Leu Ile Leu Asp Gly Glu
                20                  25                  30

Val Ser Glu Asp Trp Gln Tyr Ile Arg Lys Thr Thr Arg Glu Thr Cys
            35                  40                  45

Tyr Leu Pro Thr Lys Phe Thr Asp Thr Phe Asp Asn Leu Thr Pro Asn
    50                  55                  60

Asp Gln Asp Phe Arg Cys Asn Leu Gly Ser Phe Ser Asn Ala Ala Lys
65                  70                  75                  80

Thr Glu Val Ala Glu Val Ala Gly Ser Thr Ile Gly Met Gln Leu
                85                  90                  95

Phe Ala Gly Ser His Met Arg His Pro Gly Pro Ala Gln Val Phe Met
            100                 105                 110

Ser Lys Ala Pro Ser Gly Asn Val Gln Ser Tyr Glu Gly Asp Gly Ser
        115                 120                 125

Trp Phe Lys Ile Trp Glu Arg Thr Leu Cys Asp Lys Ser Gly Asp Leu
    130                 135                 140

Thr Gly Asp Ala Trp Cys Thr Tyr Gly Gln Thr Glu Ile Glu Phe Gln
145                 150                 155                 160

Ile Pro Glu Ala Thr Pro Thr Gly Glu Tyr Leu Val Arg Ala Glu His
                165                 170                 175

Ile Gly Leu His Arg Ala Gln Ser Asn Gln Ala Glu Phe Tyr Tyr Ser
            180                 185                 190

Cys Ala Gln Val Lys Val Thr Gly Asn Gly Thr Gly Val Pro Ser Gln
        195                 200                 205

Thr Tyr Gln Ile Pro Gly Met Tyr Asn Asp Arg Ser Glu Leu Phe Asn
    210                 215                 220

Gly Leu Asn Leu Trp Ser Tyr Ser Val Glu Asn Val Glu Ala Ala Met
225                 230                 235                 240

Lys Asn Ser Ile Val Gly Asp Glu Ile Trp Asn Gly Ser Ser Val Pro
                245                 250                 255

Ser Glu Ser His Val Pro Lys Tyr Lys Lys Ser His Ala Cys Arg Val
            260                 265                 270

Tyr

<210> SEQ ID NO 15
<211> LENGTH: 42
<212> TYPE: DNA
<213> ORGANISM: Aspergillus aculeatus

<400> SEQUENCE: 15
acacaactgg ggatccacca tgaagtatat tcctctcgtt at                                                42

<210> SEQ ID NO 16
<211> LENGTH: 37
<212> TYPE: DNA
<213> ORGANISM: Aspergillus aculeatus

<400> SEQUENCE: 16
agatctcgag aagcttagca cgaattcacg cattgat                               37

<210> SEQ ID NO 17
<211> LENGTH: 40
<212> TYPE: DNA
<213> ORGANISM: Aspergillus aculeatus

<400> SEQUENCE: 17
acacaactgg ggatccacca tgtctgttgc taagtttgct                            40

<210> SEQ ID NO 18
<211> LENGTH: 34
<212> TYPE: DNA
<213> ORGANISM: Aspergillus aculeatus

<400> SEQUENCE: 18
agatctcgag aagcttagga gaggtcacgg gcgt                                  34

<210> SEQ ID NO 19
<211> LENGTH: 40
<212> TYPE: DNA
<213> ORGANISM: Aspergillus aculeatus

<400> SEQUENCE: 19
acacaactgg ggatccacca tgaagtcctc tactttcggt                            40

<210> SEQ ID NO 20
<211> LENGTH: 35
<212> TYPE: DNA
<213> ORGANISM: Aspergillus aculeatus

<400> SEQUENCE: 20
agatctcgag aagcttaggc agactcaacg cactg                                 35

<210> SEQ ID NO 21
<211> LENGTH: 39
<212> TYPE: DNA
<213> ORGANISM: Aspergillus aculeatus

<400> SEQUENCE: 21
acacaactgg ggatccacca tgcgtcaggc tcagtctttt                             39

<210> SEQ ID NO 22
<211> LENGTH: 36
<212> TYPE: DNA
<213> ORGANISM: Aspergillus aculeatus

<400> SEQUENCE: 22
agatctcgag aagcttaggc agagatgcac tggtag                                36

<210> SEQ ID NO 23
<211> LENGTH: 40
<212> TYPE: DNA
<213> ORGANISM: Aspergillus aculeatus

<400> SEQUENCE: 23
acacaactgg ggatccacca tgtctctttc caagattgcc                            40

<210> SEQ ID NO 24
<211> LENGTH: 34
<212> TYPE: DNA
<213> ORGANISM: Aspergillus aculeatus

```
<400> SEQUENCE: 24
agatctcgag aagcttagtg acgcttggga cgcg                                    34

<210> SEQ ID NO 25
<211> LENGTH: 41
<212> TYPE: DNA
<213> ORGANISM: Aspergillus aculeatus

<400> SEQUENCE: 25
acacaactgg ggatccacca tgcttgtcaa actcatctct t                            41

<210> SEQ ID NO 26
<211> LENGTH: 35
<212> TYPE: DNA
<213> ORGANISM: Aspergillus aculeatus

<400> SEQUENCE: 26
agatctcgag aagcttaagc cgtggttgtc actgc                                   35

<210> SEQ ID NO 27
<211> LENGTH: 40
<212> TYPE: DNA
<213> ORGANISM: Aspergillus aculeatus

<400> SEQUENCE: 27
acacaactgg ggatccacca tgaagtatct tgcgatcttc                              40

<210> SEQ ID NO 28
<211> LENGTH: 38
<212> TYPE: DNA
<213> ORGANISM: Aspergillus aculeatus

<400> SEQUENCE: 28
agatctcgag aagcttatca ataaacacga caagcatg                                38
```

POLYPEPTIDES HAVING CELLULOLYTIC ENHANCING ACTIVITY AND POLYNUCLEOTIDES ENCODING SAME

CROSS-REFERENCE TO RELATED APPLICATIONS

This application is divisional application of U.S. patent application Ser. No. 13/817,754 filed on Feb. 19, 2013, now U.S. Pat. No. 9,303,074, which is a 35 U.S.C. § 371 national application of PCT/US2011/049692 filed on Aug. 30, 2011, which claims priority or the benefit under 35 U.S.C. § 119 of U.S. Provisional. Application No. 61/378,320 filed on Aug. 30, 2011, the contents of which are fully incorporated herein by reference.

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08GO18080 awarded by the Department of Energy. The government has certain rights in this invention.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having cellulolytic enhancing activity and polynucleotides encoding the polypeptides. The invention also relates to nucleic acid constructs, vectors, and host cells comprising the polynucleotides as well as methods of producing and using the polypeptides.

Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars are easily fermented by yeast into ethanol.

There is a need in the art for new polypeptides having cellulolytic enhancing activity for use in the degradation of cellulosic materials.

The present invention provides polypeptides having cellulolytic enhancing activity and polynucleotides encoding the polypeptides.

SUMMARY OF THE INVENTION

The present invention relates to isolated polypeptides having cellulolytic enhancing activity selected from the group consisting of:
(a) a polypeptide having at least 60% sequence identity to the mature polypeptide of SEQ ID NO: 2, SEQ ID NO: 6, SEQ ID NO: 12, or SEQ ID NO: 14; at least 65% sequence identity to the mature polypeptide of SEQ ID NO: 8 or SEQ ID NO: 10, or at least 75% sequence identity to the mature polypeptide of SEQ ID NO: 4;
(b) a polypeptide encoded by a polynucleotide that hybridizes under at least medium-high stringency conditions with (i) the mature polypeptide coding sequence of SEQ ID NO: 1 or the cDNA sequence thereof, SEQ ID NO: 3, SEQ ID NO: 5, SEQ ID NO: 7, SEQ ID NO: 9, SEQ ID NO: 11, or SEQ ID NO: 13 or the cDNA sequence thereof, or (ii) the full-length complement of (i);
(c) a polypeptide encoded by a polynucleotide having at least 60% sequence identity to the mature polypeptide coding sequence of SEQ ID NO: 1 or the cDNA sequence thereof, SEQ ID NO: 5, SEQ ID NO: 11, or SEQ ID NO: 13 or the cDNA sequence thereof; at least 65% sequence identity to the mature polypeptide coding sequence of SEQ ID NO: 7 or SEQ ID NO: 9, or at least 75% sequence identity to the mature polypeptide coding sequence of SEQ ID NO: 3;
(d) a variant of the mature polypeptide of SEQ ID NO: 2, SEQ ID NO: 4, SEQ ID NO: 6, SEQ ID NO: 8, SEQ ID NO: 10, SEQ ID NO: 12, or SEQ ID NO: 14 comprising a substitution, deletion, and/or insertion at one or more (e.g., several) positions; and
(e) a fragment of the polypeptide of (a), (b), (c), or (d) that has cellulolytic enhancing activity.

The present invention also relates to isolated polynucleotides encoding the polypeptides of the present invention; nucleic acid constructs, recombinant expression vectors, and recombinant host cells comprising the polynucleotides; and methods of producing the polypeptides.

The present invention also relates to processes for degrading or converting a cellulosic material, comprising: treating the cellulosic material with an enzyme composition in the presence of a polypeptide having cellulolytic enhancing activity of the present invention.

The present invention also relates to processes of producing a fermentation product, comprising: (a) saccharifying a cellulosic material with an enzyme composition in the presence of a polypeptide having cellulolytic enhancing activity of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a polypeptide having cellulolytic enhancing activity of the present invention.

The present invention also relates to a polynucleotide encoding a signal peptide comprising or consisting of amino acids 1 to 20 of SEQ ID NO: 2, amino acids 1 to 25 of SEQ ID NO: 4, amino acids 1 to 20 of SEQ ID NO: 6, amino acids 1 to 21 of SEQ ID NO: 8, amino acids 1 to 19 of SEQ ID NO: 10, amino acids 1 to 17 of SEQ ID NO: 12, or amino acids 1 to 20 of SEQ ID NO: 14, which is operably linked to a gene encoding a protein, wherein the gene is foreign to the polynucleotide encoding the signal peptide; nucleic acid constructs, expression vectors, and recombinant host cells comprising the polynucleotides; and methods of producing a protein.

DEFINITIONS

Figure 1:
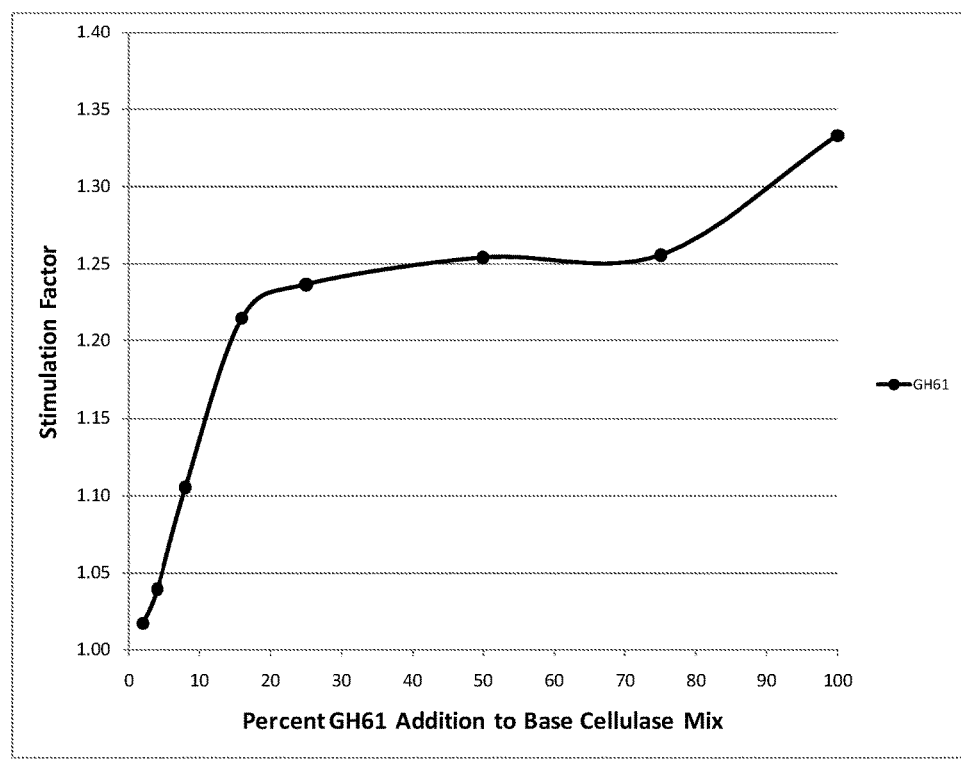
FIG. 1 shows the effect of an *Aspergillus aculeatus* P23NHW GH61 polypeptide (EXP03690) on enzymatic hydrolysis of pretreated corn stover by a *Trichoderma reesei* cellulase preparation.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 μmole of glucuronic or 4-O-methylglucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). For purposes of the present invention, cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581. In the present invention, the Lever et al. method can be employed to assess hydrolysis of cellulose in corn stover, while the methods of van Tilbeurgh et al. and Tomme et al. can be used to determine the cellobiohydrolase activity on a fluorescent disaccharide derivative, 4-methylumbelliferyl-beta-D-lactoside.

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids deleted from the amino and/or carboxyl terminus of a mature polypeptide; wherein the fragment has cellulolytic enhancing activity. In one aspect, a fragment contains at least 280 amino acid residues, e.g., at least 295 amino acid residues or at least 310 amino acid residues of SEQ ID NO: 2. In another aspect, a fragment contains at least 310 amino acid residues, e.g., at least 330 amino acid residues or at least 350 amino acid residues of SEQ ID NO: 4. In another aspect, a fragment contains at least 310 amino acid residues, e.g., at least 330 amino acid residues or at least 350 amino acid residues of SEQ ID NO: 6. In another aspect, a fragment contains at least 320 amino acid residues, e.g., at least 340 amino acid residues or at least 360 amino acid residues of SEQ ID NO: 8. In another aspect, a fragment contains at least 350 amino acid residues, e.g., at least 370 amino acid residues or at least 390 amino acid residues of SEQ ID NO: 10. In another aspect, a fragment contains at least 220 amino acid residues, e.g., at least 230 amino acid residues or at least 240 amino acid residues of SEQ ID NO: 12. In another aspect, a fragment contains at least 220 amino acid residues, e.g., at least 230 amino acid residues or at least 240 amino acid residues of SEQ ID NO: 14.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). The polypeptide of the present invention may be used in industrial applications in the form of a fermentation broth product, that is, the polypeptide of the present invention is a component of a fermentation broth used as a product in industrial applications (e.g., ethanol production). The fermentation broth product will in addition to the polypeptide of the present invention comprise additional ingredients used in the fermentation process, such as, for example, cells (including, the host cells containing the gene encoding the polypeptide of the present invention which are used to produce the polypeptide of interest), cell debris, biomass, fermentation media and/or fermentation products. The fermentation broth may optionally be subjected to one or more purification (including filtration) steps to remove or reduce one more components of a fermentation process. Accordingly, an isolated substance may be present in such a fermentation broth product.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 21 to 344 of SEQ ID NO: 2 based on the SignalP program (Nielsen et al., 1997, *Protein Engineering* 10: 1-6) that predicts amino acids 1 to 20 of SEQ ID NO: 2 are a signal peptide. In another aspect, the mature polypeptide is amino acids 26 to 400 of SEQ ID NO: 4 based on the SignalP program that predicts amino acids 1 to 25 of SEQ ID NO: 4 are a signal peptide. In another aspect, the mature polypeptide is amino acids 21 to 389 of SEQ ID NO: 6 based on the SignalP program that predicts amino acids 1 to 20 of SEQ ID NO: 6 are a signal peptide. In another aspect, the mature polypeptide is amino acids 22 to 406 of SEQ ID NO: 8 based on the SignalP program that predicts amino acids 1 to 21 of SEQ ID NO: 8 are a signal peptide. In another aspect, the mature polypeptide is amino acids 20 to 427 of SEQ ID NO: 10 based on the SignalP program that predicts amino acids 1 to 19 of SEQ ID NO: 10 are a signal peptide. In another aspect, the mature polypeptide is amino acids 18 to 267 of SEQ ID NO: 12 based on the SignalP program that predicts amino acids 1 to 17 of SEQ ID NO: 12 are a signal peptide. In another aspect, the mature polypeptide is amino acids 21 to 273 of SEQ ID NO: 14 based on the SignalP program that predicts amino acids 1 to 20 of SEQ ID NO: 14 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having cellulolytic enhancing activity. In one aspect, the mature polypeptide coding sequence is nucleotides 61 to 1032 of SEQ ID NO: 1 based on the SignalP program (Nielsen et al., 1997, supra) that predicts nucleotides 1 to 60 of SEQ ID NO: 1 encode a signal peptide. In another aspect, the mature polypeptide coding sequence is the cDNA sequence of nucleotides 61 to 1032 of SEQ ID NO: 1. In another aspect, the mature polypeptide coding sequence is nucleotides 76 to 1200 of SEQ ID NO: 3 based on the SignalP program that predicts nucleotides 1 to 75 of SEQ ID NO: 3 encode a signal peptide. In another aspect, the mature polypeptide coding sequence is nucleotides 61 to 1167 of SEQ ID NO: 5 based on the SignalP program that predicts nucleotides 1 to 60 of SEQ ID NO: 5 encode a signal peptide. In another aspect, the mature polypeptide coding sequence is nucleotides 64 to 1218 of SEQ ID NO: 7 based on the SignalP program that predicts nucleotides 1 to 63 of SEQ ID NO: 7 encode a signal peptide. In another aspect, the mature polypeptide coding sequence is nucleotides 58 to 1281 of SEQ ID NO: 9 based on the SignalP program that predicts nucleotides 1 to 57 of SEQ ID NO: 9 encode a signal peptide. In another aspect, the mature polypeptide coding sequence is nucleotides 52 to 801 of SEQ ID NO: 11 based on the SignalP program that predicts nucleotides 1 to 51 of SEQ ID NO: 11 encode a signal peptide. In another aspect, the mature polypeptide coding sequence is nucleotides 61 to 819 of SEQ ID NO: 13 based on the SignalP program that predicts nucleotides 1 to 60 of SEQ ID NO: 13 encode a signal peptide. In another aspect, the mature polypeptide coding sequence is the cDNA sequence of nucleotides 61 to 819 of SEQ ID NO: 13.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

The polypeptides of the present invention have at least 20%, e.g., at least 40%, at least 50%, at least 60%, at least 70%, at least 80%, at least 90%, at least 95%, and at least 100% of the cellulolytic enhancing activity of the mature polypeptide of SEQ ID NO: 2, SEQ ID NO: 4, SEQ ID NO: 6, SEQ ID NO: 8, SEQ ID NO: 10, SEQ ID NO: 12, or SEQ ID NO: 14.

Pretreated corn stover: The term "PCS" or "Pretreated Corn Stover" means a cellulosic material derived from corn stover by treatment with heat and dilute sulfuric acid.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0, 5.0.0, or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having cellulolytic enhancing activity. In one aspect, a subsequence contains at least 840 nucleotides, e.g., at least 885 nucleotides or at least 930 nucleotides of SEQ ID NO: 1. In another aspect, a subsequence contains at least 930 nucleotides, e.g., at least 990 nucleotides or at least 1050 nucleotides of SEQ ID NO: 3. In another aspect, a subsequence contains at least 930 nucleotides, e.g., at least 990 nucleotides or at least 1050 nucleotides of SEQ ID NO: 5. In another aspect, a subsequence contains at least 960 nucleotides, e.g., at least 1020 nucleotides or at least 1080 nucleotides of SEQ ID NO: 7. In another aspect, a subsequence contains at least 1050 nucleotides, e.g., at least 1110 nucleotides or at least 1170 nucleotides of SEQ ID NO: 9. In another aspect, a subsequence contains at least 660 nucleotides, e.g., at least 690 nucleotides or at least 720 nucleotides of SEQ ID NO: 11. In another aspect, a subsequence contains at least 660 nucleotides, e.g., at least 690 nucleotides or at least 720 nucleotides of SEQ ID NO: 13.

Variant: The term "variant" means a polypeptide having cellulolytic enhancing activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67. In the methods of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune, FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

DETAILED DESCRIPTION OF THE INVENTION

Polypeptides Having Cellulolytic Enhancing Activity

In an embodiment, the present invention relates to isolated polypeptides having a sequence identity to the mature polypeptide of SEQ ID NO: 2, SEQ ID NO: 6, SEQ ID NO: 12, or SEQ ID NO: 14 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; mature polypeptide of SEQ ID NO: 8 or SEQ ID NO: 10 of at least 65%, e.g., at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or mature polypeptide of SEQ ID NO: 4 of at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; which have cellulolytic enhancing activity. In one aspect, the polypeptides differ by up to 10 amino acids, e.g., 1, 2, 3, 4, 5, 6, 7, 8, 9, or 10, from the mature polypeptide of SEQ ID NO: 2, SEQ ID NO: 4, SEQ ID NO: 6, SEQ ID NO: 8, SEQ ID NO: 10, SEQ ID NO: 12, or SEQ ID NO: 14.

A polypeptide of the present invention preferably comprises or consists of the amino acid sequence of SEQ ID NO: 2, SEQ ID NO: 4, SEQ ID NO: 6, SEQ ID NO: 8, SEQ ID NO: 10, SEQ ID NO: 12, or SEQ ID NO: 14; or an allelic variant thereof; or is a fragment thereof having cellulolytic enhancing activity. In another aspect, the polypeptide comprises or consists of the mature polypeptide of SEQ ID NO: 2, SEQ ID NO: 4, SEQ ID NO: 6, SEQ ID NO: 8, SEQ ID NO: 10, SEQ ID NO: 12, or SEQ ID NO: 14. In another aspect, the polypeptide comprises or consists of amino acids 21 to 344 of SEQ ID NO: 2. In another aspect, the polypeptide comprises or consists of amino acids 26 to 400 of SEQ ID NO: 4. In another aspect, the polypeptide comprises or consists of amino acids 21 to 389 of SEQ ID NO: 6. In another aspect, the polypeptide comprises or consists of amino acids 22 to 406 of SEQ ID NO: 8. In another aspect, the polypeptide comprises or consists of amino acids 20 to 427 of SEQ ID NO: 10. In another aspect, the polypeptide comprises or consists of amino acids 18 to 267 of SEQ ID NO: 12. In another aspect, the polypeptide comprises or consists of amino acids 21 to 273 of SEQ ID NO: 14.

In another embodiment, the present invention relates to isolated polypeptides having cellulolytic enhancing activity that are encoded by polynucleotides that hybridize under very low stringency conditions, low stringency conditions, medium stringency conditions, medium-high stringency conditions, high stringency conditions, or very high stringency conditions with (i) the mature polypeptide coding sequence of SEQ ID NO: 1 or the cDNA sequence thereof, SEQ ID NO: 3, SEQ ID NO: 5, SEQ ID NO: 7, SEQ ID NO: 9, SEQ ID NO: 11, or SEQ ID NO: 13 or the cDNA sequence thereof, or (ii) the full-length complement of (i) (J. Sambrook, E. F. Fritsch, and T. Maniatis, 1989, *Molecular Cloning, A Laboratory Manual*, 2d edition, Cold Spring Harbor, N.Y.).

The polynucleotide of SEQ ID NO: 1, SEQ ID NO: 3, SEQ ID NO: 5, SEQ ID NO: 7, SEQ ID NO: 9, SEQ ID NO: 11, or SEQ ID NO: 13, or a subsequence thereof, as well as the amino acid sequence of SEQ ID NO: 2, SEQ ID NO: 4, SEQ ID NO: 6, SEQ ID NO: 8, SEQ ID NO: 10, SEQ ID NO: 12, or SEQ ID NO: 14, or a fragment thereof, may be used to design nucleic acid probes to identify and clone DNA encoding polypeptides having cellulolytic enhancing activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having cellulolytic enhancing activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, SEQ ID NO: 3, SEQ ID NO: 5, SEQ ID NO: 7, SEQ ID NO: 9, SEQ ID NO: 11, or SEQ ID NO: 13, or a subsequence thereof, the carrier material is used in a Southern blot.

For purposes of the present invention, hybridization indicates that the polynucleotide hybridizes to a labeled nucleic acid probe corresponding to SEQ ID NO: 1 or the cDNA sequence thereof, SEQ ID NO: 3, SEQ ID NO: 5, SEQ ID NO: 7, SEQ ID NO: 9, SEQ ID NO: 11, or SEQ ID NO: 13; the mature polypeptide coding sequence of SEQ ID NO: 1, SEQ ID NO: 3, SEQ ID NO: 5, SEQ ID NO: 7, SEQ ID NO: 9, SEQ ID NO: 11, or SEQ ID NO: 13 or the cDNA sequence thereof; the full-length complement thereof; or a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1 or the cDNA sequence thereof, SEQ ID NO: 3, SEQ ID NO: 5, SEQ ID NO: 7, SEQ ID NO: 9, SEQ ID NO: 11, or SEQ ID NO: 13 or the cDNA sequence thereof. In another aspect, the nucleic acid probe is nucleotides 61 to 1032 of SEQ ID NO: 1, nucleotides 76 to 1200 of SEQ ID NO: 3, nucleotides 61 to 1167 of SEQ ID NO: 5, nucleotides 64 to 1218 of SEQ ID NO: 7, nucleotides 58 to 1281 of SEQ ID NO: 9, nucleotides 52 to 801 of SEQ ID NO: 11, or nucleotides 61 to 819 of SEQ ID NO: 13. In another aspect, the nucleic acid probe is a polynucleotide that encodes the polypeptide of SEQ ID NO: 2, SEQ ID NO: 4, SEQ ID NO: 6, SEQ ID NO: 8, SEQ ID NO: 10, SEQ ID NO: 12, or SEQ ID NO: 14; or the mature polypeptide thereof; or a fragment thereof. In another aspect, the nucleic acid probe is SEQ ID NO: 1 or the cDNA sequence thereof, SEQ ID NO: 3, SEQ ID NO: 5, SEQ ID NO: 7, SEQ ID NO: 9, SEQ ID NO: 11, or SEQ ID NO: 13 or the cDNA sequence thereof.

In another embodiment, the present invention relates to isolated polypeptides having cellulolytic enhancing activity encoded by polynucleotides having a sequence identity to the mature polypeptide coding sequence of SEQ ID NO: 1 or the cDNA sequence thereof, SEQ ID NO: 5, SEQ ID NO: 11, or SEQ ID NO: 13 or the cDNA sequence thereof, of at least 60%, e.g., at least 65%, at least 70%, at least 75%, at least 80%, 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide coding sequence of SEQ ID NO: 7 or SEQ ID NO: 9 of at least 65%, e.g., at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or the mature polypeptide coding sequence of SEQ ID NO: 3 of at least 75%, e.g., at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2, SEQ ID NO: 4, SEQ ID NO: 6, SEQ ID NO: 8, SEQ ID NO: 10, SEQ ID NO: 12, or SEQ ID NO: 14 comprising a substitution, deletion, and/or insertion at one or more (e.g., several) positions. In an embodiment, the number of amino acid substitutions, deletions and/or insertions introduced into the mature polypeptide of SEQ ID NO: 2, SEQ ID NO: 4, SEQ ID NO: 6, SEQ ID NO: 8, SEQ ID NO: 10, SEQ ID NO: 12, or SEQ ID NO: 14 is not more than 10, e.g., 1, 2, 3, 4, 5, 6, 7, 8, 9, or 10. The, amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for cellulolytic enhancing activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, Proteins: Structure, *Function, and Genetics* 6: 240-248; and Stevens, 2003, *Drug Discovery World* 4: 35-48.

Sources of Polypeptides Having Cellulolytic Enhancing Activity

A polypeptide having cellulolytic enhancing activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. For example, the polypeptide may be a yeast polypeptide such as a *Candida*, *Kluyveromyces*, *Pichia*, *Saccharomyces*, *Schizosaccharomyces*, or *Yarrowia* polypeptide; or a filamentous fungal polypeptide such as an *Acremonium*, *Agaricus*, *Alternaria*, *Aspergillus*, *Aureobasidium*, *Botryosphaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* polypeptide.

In another aspect, the polypeptide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* polypeptide.

In another aspect, the polypeptide is an *Acremonium cellulolyticus*, *Aspergillus aculeatus*, *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium suiphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia setosa*, *Thielavia spededonium*, *Thielavia subthermophila*, *Thielavia terrestris*, *Trichoderma harzianum*, *Trichoderma koningii*, *Trichoderma longibrachiatum*, *Trichoderma reesei*, or *Trichoderma viride* polypeptide.

In another aspect, the polypeptide is an *Aspergillus aculeatus* polypeptide, e.g., a polypeptide obtained from *Aspergillus aculeatus* CBS 172.66.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide of the present invention.

The techniques used to isolate or clone a polynucleotide encoding a polypeptide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Aspergillus aculeatus*, or a related organism and thus, for example, may be an allelic or species variant of the polypeptide encoding region of the polynucleotide.

In another embodiment, the present invention relates to isolated polynucleotides comprising or consisting of polynucleotides having a degree of sequence identity to the mature polypeptide coding sequence of SEQ ID NO: 1 or the cDNA sequence thereof, SEQ ID NO: 5, SEQ ID NO: 11, or SEQ ID NO: 13 or the cDNA sequence thereof, of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide coding sequence of SEQ ID NO: 7 or SEQ ID NO: 9 of at least 65%, e.g., at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or the mature polypeptide coding sequence of SEQ ID NO: 3 of at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; which encode polypeptides having cellulolytic enhancing activity.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1 or the cDNA sequence thereof, SEQ ID NO: 3, SEQ ID NO: 5, SEQ ID NO: 7, SEQ ID NO: 9, SEQ ID NO: 11, or SEQ ID NO: 13 or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

In another embodiment, the present invention relates to isolated polynucleotides encoding polypeptides of the present invention, which hybridize under low stringency conditions, medium stringency conditions, medium-high stringency conditions, high stringency conditions, or very high stringency conditions with (i) the mature polypeptide coding sequence of SEQ ID NO: 1 or the cDNA sequence thereof, SEQ ID NO: 3, SEQ ID NO: 5, SEQ ID NO: 7, SEQ ID NO: 9, SEQ ID NO: 11, or SEQ ID NO: 13 or the cDNA sequence thereof, or (ii) the full-length complement of (i); or allelic variants and subsequences thereof (Sambrook et al., 1989, supra), as defined herein.

In one aspect, the polynucleotide comprises or consists of SEQ ID NO: 1, SEQ ID NO: 3, SEQ ID NO: 5, SEQ ID NO: 7, SEQ ID NO: 9, SEQ ID NO: 11, or SEQ ID NO: 13; or the mature polypeptide coding sequence thereof; or a subsequence thereof that encodes a fragment having cellulolytic enhancing activity.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, Scientific American 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoim idazole-succinocarboxam ide synthase), adeB (phosphor-ribosylam inoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus,* and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus,* and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In one aspect, the cell is of the genus *Aspergillus*. In another aspect, the cell is *Aspergillus aculeatus*. In another aspect, the cell is *Aspergillus aculeatus* CBS 172.66.

The present invention also relates to methods of producing a polypeptide of the present invention, comprising: (a) cultivating a recombinant host cell of the present invention under conditions conducive for production of the polypeptide; and (b) recovering the polypeptide.

The cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, the whole fermentation broth is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

Plants

The present invention also relates to isolated plants, e.g., a transgenic plant, plant part, or plant cell, comprising a polynucleotide of the present invention so as to express and produce a polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide may be constructed in accordance with methods known in the art. In short, the plant or plant cell is constructed by incorporating one or more expression constructs encoding the polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising: (a) cultivating a transgenic plant or a plant cell comprising a polynucleotide encoding the polypeptide under conditions conducive for production of the polypeptide; and (b) recovering the polypeptide.

Removal or Reduction of Cellulolytic Enhancing Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may also be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention also relates to methods of inhibiting the expression of a polypeptide having cellulolytic enhancing activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA for inhibiting transcription. In another preferred aspect, the dsRNA is micro RNA for inhibiting translation.

The present invention also relates to such double-stranded RNA (dsRNA) molecules, comprising a portion of the mature polypeptide coding sequence of SEQ ID NO: 1, SEQ ID NO: 3, SEQ ID NO: 5, SEQ ID NO: 7, SEQ ID NO: 9, SEQ ID NO: 11, or SEQ ID NO: 13 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for expression of native and heterologous polypeptides. Therefore, the present invention further relates to methods of producing a native or heterologous polypeptide, comprising: (a) cultivating the mutant cell under conditions conducive for production of the polypeptide; and (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially cellulolytic enhancing-free product is of particular interest in the production of eukaryotic polypeptides, in particular fungal proteins such as enzymes. The cellulolytic enhancing-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from cellulolytic enhancing activity that is produced by a method of the present invention.

Compositions

The present invention also relates to compositions comprising a polypeptide of the present invention. Preferably, the compositions are enriched in such a polypeptide. The term "enriched" indicates that the cellulolytic enhancing activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (several) enzymes selected from the group consisting of a cellulase, a hemicellulase, an expansin, an esterase, a laccase, a ligninolytic enzyme, a pectinase, a peroxidase, a protease, and a swollenin.

The compositions may be prepared in accordance with methods known in the art and may be in the form of a liquid or a dry composition. The polypeptide to be included in the composition may be stabilized in accordance with methods known in the art.

The compositions may be a fermentation broth formulation or a cell composition, as described herein. Consequently, the present invention also relates to fermentation broth formulations and cell compositions comprising a polypeptide having cellulolytic enhancing activity of the present invention. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compostions may further comprise a preservative and/or anti-microbial (e.g., bacteriostatic) agent, including, but not limited to, sorbitol, sodium chloride, potassium sorbate, and others known in the art.

The cell-killed whole broth or composition may further comprise one or more enzyme activities such as cellobiohydrolase, endoglucanase, beta-glucosidase, endo-beta-1,3 (4)-glucanase, glucohydrolase, xyloglucanase, xylanase, xylosidase, arabinofuranosidase, alpha-glucuronidase, acetyl xylan esterase, mannanase, mannosidase, alpha-galactosidase, mannan acetyl esterase, galactanase, arabinanase, pectate lyase, pectinase lyase, pectate lyase, polygalacturonase, pectin acetyl esterase, pectin methyl esterase, beta-galactosidase, galactanase, arabinanase, alpha-arabinofuranosidase, rhamnogalacturonase, ferrulic acid esterases rhamnogalacturonan lyase, rhamnogalacturonan acetyl esterase, xylogalacturonosidase, xylogalacturonase, rhamnogalacturonan lyase, lignin peroxidases, manganese-dependent peroxidases, hybrid peroxidases, with combined properties of lignin peroxidases and manganese-dependent peroxidases, glucoamylase, amylase, protease, and laccase.

In some embodiments, the cell-killed whole broth or composition includes cellulolytic enzymes including, but not limited to, (i) endoglucanases (EG) or 1,4-D-glucan-4-glucanohydrolases (EC 3.2.1.4), (ii) exoglucanases, including 1,4-D-glucan glucanohydrolases (also known as cellodextrinases) (EC 3.2.1.74) and 1,4-D-glucan cellobiohydrolases (exo-cellobiohydrolases, CBH) (EC 3.2.1.91), and (iii) beta-glucosidase (BG) or beta-glucoside glucohydrolases (EC 3.2.1.21).

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Uses

The present invention is also directed to the following processes for using the polypeptides having cellulolytic enhancing activity, or compositions thereof.

The present invention also relates to processes for degrading a cellulosic material, comprising: treating the cellulosic material with an enzyme composition in the presence of a polypeptide having cellulolytic enhancing activity of the present invention. In one aspect, the processes further comprise recovering the degraded or converted cellulosic material. Soluble products of degradation or conversion of the cellulosic material can be separated from insoluble cellulosic material using a method known in the art such as, for example, centrifugation, filtration, or gravity settling.

The present invention also relates to processes of producing a fermentation product, comprising: (a) saccharifying a cellulosic material with an enzyme composition in the presence of a polypeptide having cellulolytic enhancing activity of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a polypeptide having cellulolytic enhancing activity of the present invention. In one aspect, the fermenting of the cellulosic material produces a fermentation product. In another aspect, the processes further comprise recovering the fermentation product from the fermentation.

The processes of the present invention can be used to saccharify the cellulosic material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material typically involves pretreatment, enzymatic hydrolysis (saccharification), and fermentation.

The processing of the cellulosic material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bio-ethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment. In practicing the processes of the present invention, any pretreatment process known in the art can be used to disrupt plant cell wall components of the cellulosic material (Chandra et al., 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt %, e.g., 20-70 wt % or 30-60 wt %, such as around 40 wt %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in Enzymatic Conversion of Biomass for Fuels Production, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification. In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition as described herein in the presence of a polypeptide having cellulolytic enhancing activity of the present invention. The enzymes of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can comprise any protein useful in degrading the cellulosic material.

In one aspect, the enzyme composition comprises or further comprises one or more (e.g., several) proteins selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin.

In the processes of the present invention, the enzyme(s) can be added prior to or during fermentation, e.g., during saccharification or during or after propagation of the fermenting microorganism(s).

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and a polypeptide having cellulolytic enhancing activity depend on several factors including, but not limited to, the mixture of component cellulolytic enzymes, the cellulosic material, the concentration of cellulosic material, the pretreatment(s) of the cellulosic material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another aspect, an effective amount of a polypeptide having cellulolytic enhancing activity to the cellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material.

In another aspect, an effective amount of a polypeptide having cellulolytic enhancing activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material, e.g., GH61 polypeptides having cellulolytic enhancing activity (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia,* or *Oceanobacillus* polypeptide having enzyme activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having enzyme activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having enzyme activity.

In another aspect, the polypeptide is a *Streptococcus equisimilis, Streptococcus pyogenes, Streptococcus uberis,* or *Streptococcus equi* subsp. *Zooepidemicus* polypeptide having enzyme activity.

In another aspect, the polypeptide is a *Streptomyces achromogenes, Streptomyces avermitilis, Streptomyces coelicolor, Streptomyces griseus,* or *Streptomyces lividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces,* or *Yarrowia* polypeptide having enzyme activity; or more preferably a filamentous fungal polypeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having enzyme activity.

In one aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having enzyme activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride,* or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the processes of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, *Gene* 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia carotovara* endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637).

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 5,457,046, U.S. Pat. No. 5,648,263, and U.S. Pat. No. 5,686,593.

In one aspect, the GH61 polypeptide having cellulolytic enhancing activity is used in the presence of a soluble activating divalent metal cation according to WO 2008/151043, e.g., manganese sulfate.

In one aspect, the GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothienopyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of thenitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™

333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8X212).

Examples of acetylxylan esterases useful in the processes of the present invention include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number Q0UHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt accession number alcc12), *Aspergillus fumigatus* (SwissProt accession number Q4WW45), *Aspergillus niger* (Uniprot accession number Q96WX9), *Aspergillus terreus* (SwissProt accession number QOCJP9), *Humicola insolens* (WO 2010/014706), *Penicillium aurantiogriseum* (WO 2009/068565), *Talaromyces emersonii* (UniProt accession number Q8X211), and *Trichoderma reesei* (Uniprot accession number Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, C A, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation. The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida, Kluyveromyces*, and *Saccharomyces*, e.g., *Candida sonorensis, Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans*, *Clostridium acetobutylicum*, *Clostridium thermocellum*, *Clostridium phytofermentans*, *Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans*; *Candida*, such as *C. sonorensis*, *C. methanosorbosa*, *C. diddensiae*, *C. parapsilosis*, *C. naedodendra*, *C. blankii*, *C. entomophilia*, *C. brassicae*, *C. pseudotropicalis*, *C. boidinii*, *C. utilis*, and *C. scehatae*; *Clostridium*, such as *C. acetobutylicum*, *C. thermocellum*, and *C. phytofermentans*; *E. coli*, especially *E. coli* strains that have been genetically modified to improve the yield of ethanol; *Geobacillus* sp.; *Hansenula*, such as *Hansenula anomala*; *Klebsiella*, such as *K. oxytoca*; *Kluyveromyces*, such as *K. marxianus*, *K. lactis*, *K. thermotolerans*, and *K. fragilis*; *Schizosaccharomyces*, such as *S. pombe*; *Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacillus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the processes of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation products: A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol.

13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptides

The present invention also relates to an isolated polynucleotide encoding a signal peptide comprising or consisting of amino acids 1 to 20 of SEQ ID NO: 2, amino acids 1 to 25 of SEQ ID NO: 4, amino acids 1 to 20 of SEQ ID NO: 6, amino acids 1 to 21 of SEQ ID NO: 8, amino acids 1 to 19 of SEQ ID NO: 10, amino acids 1 to 17 of SEQ ID NO: 12, or amino acids 1 to 20 of SEQ ID NO: 14. The polynucleotides may further comprise a gene encoding a protein, which is operably linked to the signal peptide. The protein is preferably foreign to the signal peptide.

The present invention also relates to nucleic acid constructs, expression vectors and recombinant host cells comprising such polynucleotides.

The present invention also relates to methods of producing a protein, comprising: (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone or variant thereof, enzyme, receptor or portion thereof, antibody or portion thereof, or reporter. For example, the protein may be an oxidoreductase, transferase, hydrolase, lyase, isomerase, or ligase such as an am inopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples that should not be construed as limiting the scope of the invention.

EXAMPLES

Materials

Chemicals used as buffers and substrates were commercial products of at least reagent grade.

Strains

*Aspergillus aculeatus* CBS 172.66 was used as the source of polypeptides having cellulolytic enhancing activity. *Aspergillus oryzae* MT3568 strain was used for expression of the *A. aculeatus* genes encoding the polypeptides having cellulolytic enhancing activity. *A. oryzae* MT3568 is an amdS (acetamidase) disrupted gene derivative of *Aspergillus oryzae* JaL355 (WO 2002/40694) in which pyrG auxotrophy was restored by disrupting the *A. oryzae* acetamidase (amdS) gene with the pyrG gene.

Media and Solutions

YP+2% glucose medium was composed of 1% yeast extract, 2% peptone and 2% glucose.

YP+2% maltodextrin medium was composed of 1% yeast extract, 2% peptone and 2% maltodextrin.

PDA agar plates were composed of potato infusion (potato infusion was made by boiling 300 g of sliced (washed but unpeeled) potatoes in water for 30 minutes and then decanting or straining the broth through cheesecloth. Distilled water was then added until the total volume of the suspension was one liter, followed by 20 g of dextrose and 20 g of agar powder. The medium was sterilized by autoclaving at 15 psi for 15 minutes (Bacteriological Analytical Manual, 8th Edition, Revision A, 1998).

LB plates were composed of 10 g of Bacto-Tryptone, 5 g of yeast extract, 10 g of sodium chloride, 15 g of Bacto-agar, and deionized water to 1 liter.

LB medium was composed of 10 g of Bacto-Tryptone, 5 g of yeast extract, 10 g of sodium chloride, and deionized water to 1 liter.

COVE sucrose plates were composed of 342 g of sucrose, 20 g of agar powder, 20 ml of COVE salts solution, and deionized water to 1 liter. The medium was sterilized by autoclaving at 15 psi for 15 minutes (Bacteriological Analytical Manual, 8th Edition, Revision A, 1998). The medium was cooled to 60° C. and 10 mM acetamide, 15 mM CsCl, TRITON® X-100 (50 µl/500 ml) were added.

COVE salts solution was composed of 26 g of $MgSO_4.7H_2O$, 26 g of KCL, 26 g of $KH_2PO_4$, 50 ml of COVE trace metals solution, and deionized water to 1 liter.

COVE trace metals solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_4.2H_2O$, 10 g of $ZnSO_4.7H_2O$, and deionized water to 1 liter.

Example 1: Source of DNA Sequence Information for *Aspergillus aculeatus* CBS 172.66

Genomic sequence information was generated by the U.S. Department of Energy Joint Genome Institute (JGI). A preliminary assembly of the genome was downloaded from JGI and analyzed using the Pedant-Pro™ Sequence Analysis Suite (Biomax Informatics AG, Martinsried, Germany). Gene models constructed by the software were used as a starting point for detecting GH61 homologues in the genome. More precise gene models were constructed manually using multiple known GH61 protein sequences as a guide.

Example 2: *Aspergillus aculeatus* CBS 172.66 Genomic DNA Extraction

*Aspergillus aculeatus* CBS 172.66 was propagated on PDA agar plates at 26° C. for 7 days. Spores harvested from the PDA plates were used to inoculate 25 ml of YP+2% glucose medium in a baffled shake flask and incubated at 26° C. for 48 hours with agitation at 200 rpm.

Genomic DNA was isolated according to a modified FASTDNA® SPIN protocol (Qbiogene, Inc., Carlsbad, Calif., USA). Briefly a FASTDNA® SPIN Kit for Soil (Qbiogene, Inc., Carlsbad, Calif., USA) was used in a FASTPREP® 24 Homogenization System (MP Biosciences, Santa Ana, Calif., USA). Two ml of fungal material from the above culture was harvested by centrifugation at 14,000×g for 2 minutes. The supernatant was removed and the pellet resuspended in 500 µl of deionized water. The suspension was transferred to a Lysing Matrix E FASTPREP® tube (Qbiogene, Inc., Carlsbad, Calif., USA) and 790 µl of sodium phosphate buffer and 100 µl of MT buffer from the FASTDNA® SPIN Kit were added to the tube. The sample was then secured in the FASTPREP® Instrument (Qbiogene, Inc., Carlsbad, Calif., USA) and processed for 60 seconds at a speed of 5.5 m/sec. The sample was then centrifuged at 14,000×g for two minutes and the supernatant transferred to a clean EPPENDORF® tube. A 250 µl volume of PPS reagent from the FASTDNA® SPIN Kit was added and then the sample was mixed gently by inversion. The sample was again centrifuged at 14,000×g for 5 minutes. The supernatant was transferred to a 15 ml tube followed by 1 ml of Binding Matrix suspension from the FASTDNA® SPIN Kit and then mixed by inversion for two minutes. The sample was placed in a stationary tube rack and the silica matrix was allowed to settle for 3 minutes. A 500 µl volume of the supernatant was removed and discarded and then the remaining sample was resuspended in the matrix. The sample was then transferred to a SPIN filter tube from the FASTDNA® SPIN Kit and centrifuged at 14,000×g for 1 minute. The catch tube was emptied and the remaining matrix suspension added to the SPIN filter tube. The sample was again centrifuged at 14,000×g for 1 minute. A 500 µl volume of SEWS-M solution from the FASTDNA® SPIN Kit was added to the SPIN filter tube and the sample was centrifuged at the same speed for 1 minute. The catch tube was emptied and the SPIN filter replaced in the catch tube. The unit was centrifuged at 14,000×g for 2 minutes to dry the matrix of residual SEWS-M wash solution. The SPIN filter was placed in a fresh catch tube and allowed to air dry for 5 minutes at room temperature. The matrix was gently resuspended in 100 µl of DES (DNase/Pyrogen free water) with a pipette tip. The unit was centrifuged at 14,000×g for 1 minute to elute the genomic DNA followed by elution with 100 µl of 0.1 mM EDTA-10 mM Tris pH 8.0 by centrifugation at 14,000×g for 1 minute and the eluates were combined. The concentration of the DNA harvested from the catch tube was measured at 260 nm with a UV spectrophotometer.

Example 3: Construction of an *Aspergillus oryzae* Expression Vector Containing *Aspergillus aculeatus* CBS 172.66 Genomic Sequence Encoding a GH61 Polypeptide Having Cellulolytic Enhancing Activity Two synthetic oligonucleotide primers shown below were designed to amplify by PCR the *Aspergillus aculeatus* CBS 172.66 P23NNT GH61 gene from the genomic DNA prepared in Example 2. An IN-FUSION® Cloning Kit (Clontech Laboratories, Inc., Mountain View, Calif., USA) was used to clone the fragment directly into the expression vector pDau109 (WO 2005/042735).

```
Primer F-P23NNT:
                                        (SEQ ID NO: 15)
5'-ACACAACTGGGGATCCACCATGAAGTATATTCCTCTCGTTAT-3'

Primer R-P23NNT:
                                        (SEQ ID NO: 16)
5'-AGATCTCGAGAAGCTTAGCACGAATTCACGCATTGAT-3'
```

Bold letters represent coding sequence. The underlined sequence is homologous to insertion sites of pDau109.

The PCR reaction was composed of 20 µl of Extensor Long PCR Master Mix (AB Gene Ltd., Epsom United Kingdom), Buffer 1 (AB Gene Ltd., Epsom United Kingdom), REDDYMIX™ Version (AB Gene Ltd., Epsom United Kingdom), 1 µl of primer F-P23NN (100 µM), 1 µl of primer R-P23NNT (100 µM), 1 µl of *A. aculeatus* genomic DNA (100 ng/µl of 1 mM EDTA-10 mM Tris pH 8.0), and 17 µl of deionized water in a total volume of 40 µl. The master mix contains buffer, dNTPs and a thermostable DNA polymerase blend. The PCR was performed in a PTC-200 DNA engine (MJ Research Inc., Waltham, Mass., USA) programmed for 1 cycle at 95° C. for 2 minutes. 30 cycles each at 94° C. for 10 seconds, 55° C. for 30 seconds, and 68° C. for 1 minute; and 1 cycle at 68° C. for 10 minutes. The sample was then held at 10° C. until removed from the PCR machine.

The reaction products were isolated by 1.0% agarose gel electrophoresis using 40 mM Tris base, 20 mM sodium acetate, 1 mM disodium EDTA (TAE) buffer where a 1068 bp product band was excised from the gel and purified using an illustra GFX® PCR DNA and Gel Band Purification Kit (GE Healthcare Life Sciences, Brondby, Denmark) according to the manufacturer's instructions. The fragment was then cloned into Hind III and Bam HI digested pDau109 using an IN-FUSION® Cloning Kit resulting in plasmid pP23NNT. Cloning of the P23NNT gene into Hind III-Bam HI digested pDau109 resulted in transcription of the *Aspergillus aculeatus* P23NNT gene under the control of a NA2-tpi double promoter. The NA2-tpi promoter is a modified promoter from the gene encoding the *Aspergillus niger* neutral alpha-amylase in which the untranslated leader has been replaced by an untranslated leader from the gene encoding the *Aspergillus nidulans* triose phosphate isomerase.

The cloning protocol was performed according to the IN-FUSION® Cloning Kit instructions generating a P23NNT GH61 construct. The treated plasmid and insert were transformed into FUSION BLUE™ *E. coli* cells (Clontech Laboratories, Inc., Mountain View, Calif., USA) according to the manufacturer's protocol and plated onto LB plates supplemented with 50 μg of ampicillin per ml. After incubating at 37° C. overnight, colonies were observed growing under selection on the LB ampicillin plates. Ten colonies transformed with the P23NNT GH61 construct were cultivated in LB medium supplemented with 50 μg of ampicillin per ml and plasmid DNA was isolated using a JETQUICK™ Plasmid Purification Spin Kit (GENOMED GmbH, Löhne, Germany) according to the manufacturer's instructions.

The isolated plasmids were sequenced with vector primers and P23NNT gene specific primers in order to determine a representative plasmid expression clone that was free of PCR errors.

The pairs of synthetic oligonucleotide primers shown below were designed to PCR amplify the *A. aculeatus* CBS 172.66 P23NK1 GH61 gene, P23NJS GH61 gene, P23NNN GH61 gene, and P23NHW GH61 gene from the *A. aculeatus* genomic DNA using the same procedure described above for the P23NNT GH61 gene.

```
P23NK1 GH61 gene
Primer F-P23NK1:
                                      (SEQ ID NO: 19)
5'-ACACAACTGGGGATCCACCATGAAGTCCTCTACTTTCGGT-3'

Primer R-P23NK1:
                                      (SEQ ID NO: 20)
5'-AGATCTCGAGAAGCTTAGGCAGACTCAACGCACTG-3'

P23NJS GH61 gene
Primer F-P23NJS:
                                      (SEQ ID NO: 21)
5'-ACACAACTGGGGATCCACCATGCGTCAGGCTCAGTCTTT-3'

Primer R-P23NJS:
                                      (SEQ ID NO: 22)
5'-AGATCTCGAGAAGCTTAGGCAGAGATGCACTGGTAG-3'

P23NNN GH61 gene
Primer F-P23NNN:
                                      (SEQ ID NO: 23)
5'-ACACAACTGGGGATCCACCATGTCTCTTTCCAAGATTGCC-3'

Primer R-P23NNN:
                                      (SEQ ID NO: 24)
5'-AGATCTCGAGAAGCTTAGTGACGCTTGGGACGCG-3'

P23NHW GH61 gene
Primer F-P23NHW:
                                      (SEQ ID NO: 25)
5'-ACACAACTGGGGATCCACCATGCTTGTCAAACTCATCTCTT-3'

Primer R-P23NHW:
                                      (SEQ ID NO: 26)
5'-AGATCTCGAGAAGCTTAAGCCGTGGTTGTCACTGC-3'
```

Bold letters represent coding sequence. The underlined sequence is homologous to insertion sites of pDau109.

The pairs of synthetic oligonucleotide primers shown below were designed to PCR amplify the *A. aculeatus* CBS 172.66 P23NJ4 gene and P23NQ3 GH61 gene from the *A. aculeatus* genomic DNA using the same procedure described above for the P23NNT GH61 gene.

```
P23NJ4 GH61 gene
Primer F-P23NJ4:
                                      (SEQ ID NO: 17)
5'-ACACAACTGGGGATCCACCATGTCTGTTGCTAAGTTTGCT-3'

Primer R-P23NJ4:
                                      (SEQ ID NO: 18)
5'-AGATCTCGAGAAGCTTAGGAGAGGTCACGGGCGT-3'

P23NQ3 GH61 gene
Primer F-P23NQ3:
                                      (SEQ ID NO: 27)
5'-ACACAACTGGGGATCCACCATGAAGTATCTTGCGATCTTC-3'

Primer R-P23NQ3:
                                      (SEQ ID NO: 28)
AGATCTCGAGAAGCTTATCAATAAACACGACAAGCATG-3'
```

Bold letters represent coding sequence. The underlined sequence is homologous to the insertion sites of pDau109.

Example 4: Characterization of *Aspergillus aculeatus* CBS 172.66 Genomic Sequences Encoding GH61 Polypeptides Having Cellulolytic-Enhancing Activity DNA sequencing of the *Aspergillus aculeatus* CBS 172.66 GH61 genomic clones was performed with an Applied Biosystems Model 3700 Automated DNA Sequencer using version 3.1 BIG-DYE™ terminator chemistry (Applied Biosystems, Inc., Foster City, Calif., USA) and primer walking strategy. Nucleotide sequence data were scrutinized for quality and all sequences were compared to each other with assistance of PHRED/PHRAP software (University of Washington, Seattle, Wash., USA).

The nucleotide sequence and deduced amino acid sequence of the *Aspergillus aculeatus* P23NNT GH61 gene are shown in SEQ ID NO: 1 and SEQ ID NO: 2, respectively. The coding sequence is 1200 bp including the stop codon and is interrupted by introns of 85 bp (nucleotides 332 to 416) and 80 bp (nucleotides 661 to 740). The encoded predicted protein is 344 amino acids. Using the SignalP program (Nielsen et al., 1997, *Protein Engineering* 10: 1-6), a signal peptide of 20 residues was predicted. The predicted mature protein contains 324 amino acids.

A comparative pairwise global alignment of amino acid sequences was determined using the Needleman and Wunsch algorithm (Needleman and Wunsch, 1970, *J. Mol. Biol.* 48: 443-453) with gap open penalty of 10, gap extension penalty of 0.5, and the EBLOSUM62 matrix. The alignment showed that the deduced amino acid sequence of the *Aspergillus aculeatus* gene encoding the P23NNT GH61 polypeptide shares 18% identity (excluding gaps) to the deduced amino acid sequence of a GH61 family protein from *Thermoascus aurantiacus* (accession number GENESEQP: AEC05922).

The nucleotide sequence and deduced amino acid sequence of the *Aspergillus aculeatus* P23NJ4 GH61 gene are shown in SEQ ID NO: 3 and SEQ ID NO: 4, respectively. The coding sequence is 1203 bp including the stop codon and contains no introns. The encoded predicted protein is 400 amino acids. Using the SignalP program (Nielsen et al., 1997, supra), a signal peptide of 25 residues was predicted. The predicted mature protein contains 375 amino acids.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Aspergillus aculeatus* gene encoding the P23NJ4 GH61 polypeptide shares 73.8% identity (excluding gaps) to the deduced amino acid sequence of a GH61 family protein from *Thermoascus aurantiacus* (accession number GENESEQP:AECO5922).

The nucleotide sequence and deduced amino acid sequence of the *Aspergillus aculeatus* P23NK1 GH61 gene are shown in SEQ ID NO: 5 and SEQ ID NO: 6, respectively. The coding sequence is 1170 bp including the stop codon and contains no introns. The encoded predicted protein is 389 amino acids. Using the SignalP program (Nielsen et al., 1997, supra), a signal peptide of 20 residues was predicted. The predicted mature protein contains 369 amino acids.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Aspergillus aculeatus* gene encoding the P23NK1 GH61 polypeptide shares 32% identity (excluding gaps) to the deduced amino acid sequence of a GH61 family protein from *Thermoascus aurantiacus* (accession number GENESEQP:AECO5922).

The nucleotide sequence and deduced amino acid sequence of the *Aspergillus aculeatus* P23NJS GH61 gene are shown in SEQ ID NO: 7 and SEQ ID NO: 8, respectively. The coding sequence is 1221 bp including the stop codon and contains no introns. The encoded predicted protein is 406 amino acids. Using the SignalP program (Nielsen et al., 1997, supra), a signal peptide of 21 residues was predicted. The predicted mature protein contains 385 amino acids.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Aspergillus aculeatus* gene encoding the P23NJS GH61 polypeptide shares 60% identity (excluding gaps) to the deduced amino acid sequence of a GH61 family protein from *Thermoascus aurantiacus* (accession number GENESEQP:AECO5922).

The nucleotide sequence and deduced amino acid sequence of the *Aspergillus aculeatus* P23NNN GH61 gene are shown in SEQ ID NO: 9 and SEQ ID NO: 10, respectively. The coding sequence is 1284 bp including the stop codon and contains no introns. The encoded predicted protein is 427 amino acids. Using the SignalP program (Nielsen et al., 1997, supra), a signal peptide of 19 residues was predicted. The predicted mature protein contains 408 amino acids.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Aspergillus aculeatus* gene encoding the P23NNN GH61 polypeptide shares 62% identity (excluding gaps) to the deduced amino acid sequence of a GH61 family protein from *Thermoascus aurantiacus* (accession number GENESEQP:AECO5922).

The nucleotide sequence and deduced amino acid sequence of the *Aspergillus aculeatus* P23NHW GH61 gene are shown in SEQ ID NO: 11 and SEQ ID NO: 12, respectively. The coding sequence is 804 bp including the stop codon and contains no introns. The encoded predicted protein is 267 amino acids. Using the SignalP program (Nielsen et al., 1997, supra), a signal peptide of 17 residues was predicted. The predicted mature protein contains 250 amino acids.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Aspergillus aculeatus* gene encoding the P23NHW GH61 polypeptide shares 59% identity (excluding gaps) to the deduced amino acid sequence of a GH61 family protein from *Thermoascus aurantiacus* (accession number GENESEQP:AECO5922).

The nucleotide sequence and deduced amino acid sequence of the *Aspergillus aculeatus* P23NQ3 GH61 gene are shown in SEQ ID NO: 13 and SEQ ID NO: 14, respectively. The coding sequence is 822 bp including the stop codon and is interrupted by introns of 95 bp (nucleotides 332 to 426) and 64 bp (nucleotides 671 to 734). The encoded predicted protein is 273 amino acids. Using the SignalP program (Nielsen et al., 1997, supra), a signal peptide of 20 residues was predicted. The predicted mature protein contains 253 amino acids.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Aspergillus aculeatus* gene encoding the P23NQ3 GH61 polypeptide shares 18% identity (excluding gaps) to the deduced amino acid sequence of a GH61 family protein from *Thermoascus aurantiacus* (accession number GENESEQP:AECO5922).

Example 5: Expression of *Aspergillus aculeatus* CBS 172.66 Family 61 Glycosyl Hydrolase P23NNT Gene in *Aspergillus oryzae* MT3568

One error-free pP23NNT clone comprising the P23NNT GH61 gene of SEQ ID NO: 1 was selected for further work. Plasmid DNA was then isolated using a JETSTAR 2.0 Plasmid Mini/Midi/Maxi-Protocol (Genomed). The purified plasmid DNA was transformed into protoplasts of *Aspergillus oryzae* MT3568, which were prepared according to the method of Christensen et al., 1988, *Bio/Technology* 6: 1419-1422. The selection plates consisted of COVE sucrose+10 mM acetamide+15 mM CsCl+TRITON® X-100 (50 µl/500 ml). The plates were incubated at 37° C. The transformation of *A. oryzae* MT3568 with pP23NNT yielded several transformants. Eight transformants were inoculated into separate wells of a 96 microtiter deep well plate (Nunc A/S, Roskilde, Denmark) with each well containing 750 µl of YP+2% glucose medium or 750 µl of YP+2% maltodextrin. The plate was covered with Nunc prescored vinyl sealing tape (ThermoFisher Scientific, Roskilde, Denmark) and incubated at 26° C. stationary for 4 days. The colonies on the selection plates were also restreaked onto COVE sucrose (+10 mM acetamide+15 mM CsCl+TRITON® X-100 (50

μl/500 ml)). The plates were incubated at 37° C. and this selection procedure was repeated in order to stabilize the transformants.

Several *Aspergillus oryzae* transformants produced the recombinant P23NNT GH61 polypeptide of SEQ ID NO: 2 as judged by SDS-PAGE analysis.

Error-free clones for pP23NJS comprising the P23NJS GH61 gene, pP23NNN comprising the P23NNN GH61 gene, pP23NK1 comprising the P23NK1GH61 gene, pP23NHW comprising the P23NHW GH61 gene, pP23NJ4 comprising the P23NJ4 GH61 gene, and pP23NQ3 comprising the P23NQ3 GH61 gene were transformed into *A. oryzae* MT3568 using the same procedure above.

One *Aspergillus oryzae* transformant for each of the P23NHW GH61 gene (EXP03690), P23NJS GH61 gene (EXP03691), P23NNN GH61 gene (EXP03692), and P23NK1 GH61 gene (EXP03693) was streaked onto PDA plates and incubated at 34° C. for two weeks. Spores were removed in 5 ml of 0.01% TWEEN® 20 and 4 ml of spore suspension was inoculated into 500 ml of YP+2% glucose medium, and incubated at 28° C. for 4 days with shaking at 250 rpm. The supernatants were harvested by filtering through a 0.22 μm filter.

Example 6: Effect of *Aspergillus aculeatus* GH61 Polypeptides on Hydrolysis of Pretreated Corn Stover The filtered supernatants (Example 5) from the *Aspergillus oryzae* transformants for the P23NHW GH61 gene (EXP03690), P23NJS GH61 gene (EXP03691), P23NNN GH61 gene (EXP03692), and P23NK1 GH61 gene (EXP03693) were concentrated approximately 20-fold using an Amicon ultrafiltration device (Millipore, Bedford, Mass., USA, 10 kDa polyethersulfone membrane, 40 psi, 4° C.). Protein concentration was determined by a BCA Protein Assay (BCA Protein Assay Kit, Thermo Fisher Scientific, Waltham, Mass., USA). Corn stover was pretreated and prepared as an assay substrate as described in WO 2005/074647 to generate pretreated corn stover (PCS). The base cellulase mixture used to assay enhancing activity was prepared from *Trichoderma reesei* strain SMA135 (WO 2008/057637).

Hydrolysis of PCS was conducted using 1.6 ml deep-well plates (Axygen, Santa Clara, Calif., USA) with a total reaction volume of 1.0 ml and a PCS concentration of 50 mg/ml in 1 mM manganese sulfate-50 mM sodium acetate pH 5.0. The *Aspergillus aculeatus* GH61 polypeptide was separately added to the base cellulase mixture at concentrations ranging from 0 to 100% of the protein concentration of the base cellulase mixture. Incubation was at 50° C. for 72 hours. Assays were performed in triplicate. Aliquots were centrifuged, and the supernatant liquid was filtered by centrifugation (MULTISCREEN® HV 0.45 μm, Millipore, Billerica, Mass., USA) at 3000 rpm for 10 minutes using a plate centrifuge (SORVALL® RT7, Thermo Fisher Scientific, Waltham, Mass., USA). When not used immediately, filtered hydrolysate aliquots were frozen at −20° C. Sugar concentrations of samples diluted in 0.005 M $H_2SO_4$ with 0.05% w/w benzoic acid were measured after elution by 0.005 M $H_2SO_4$ with 0.05% w/w benzoic acid at a flow rate of 0.6 ml/minute from a 4.6×250 mm AMINEX® HPX-87H column (Bio-Rad Laboratories, Inc., Hercules, Calif., USA) at 65° C. with quantitation by integration of glucose and cellobiose signals from refractive index detection (CHEMSTATION®, AGILENT® 1100 HPLC, Agilent Technologies, Santa Clara, Calif., USA) calibrated by pure sugar samples (Absolute Standards Inc., Hamden, Conn., USA). The resultant equivalents were used to calculate the percentage of cellulose conversion for each reaction. The degree of cellulose conversion to glucose plus cellobiose sugars (conversion, %) was calculated using the following equation:

Conversion (%)=(glucose+cellobiose×1.053)(mg/ml)×100×162/(Cellulose(mg/ml)×180)=(glucose+cellobiose×1.053)(mg/ml)×100/(Cellulose (mg/ml)×1.111)

In this equation the factor 1.111 reflects the weight gain in converting cellulose to glucose, and the factor 1.053 reflects the weight gain in converting cellobiose to glucose. Cellulose in PCS was determined by a limit digest of PCS to release glucose and cellobiose.

The result of adding increasing amounts of the *Aspergillus aculeatus* P23NHW GH61 polypeptide (EXP03690) to the base cellulase mix are shown in FIG. 1. Addition of the *Aspergillus aculeatus* GH61 polypeptide provided a stimulation factor of 1.33 at a 100% addition level.

Figure 2:
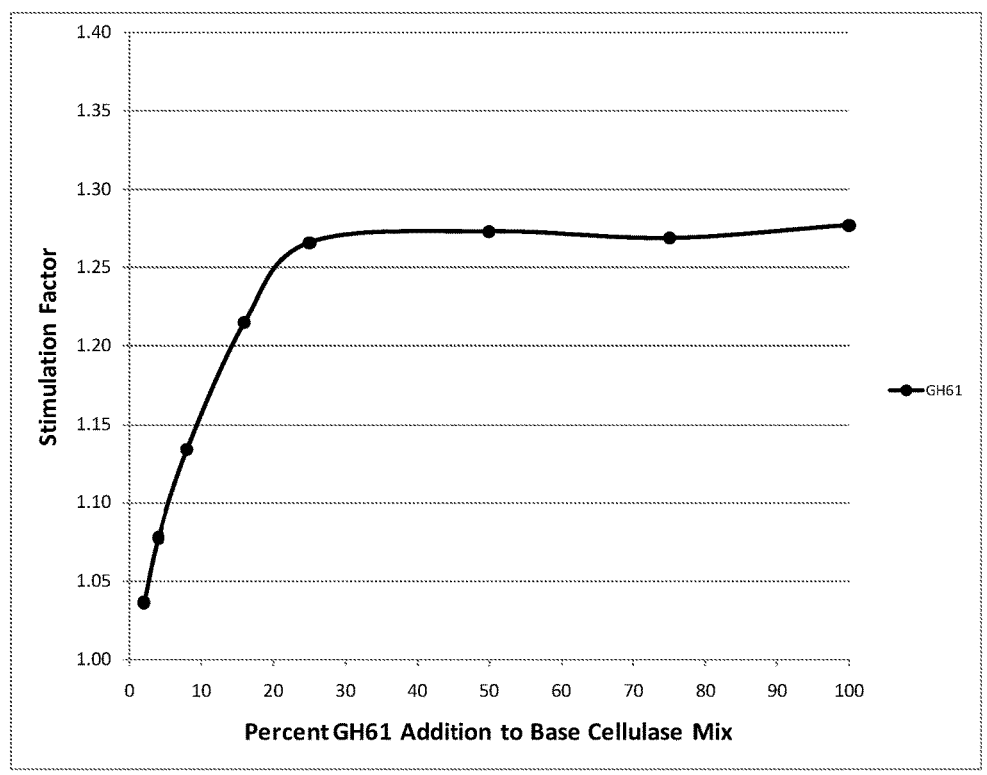
FIG. 2 shows the effect of an *Aspergillus aculeatus* P23NJS GH61 polypeptide (EXP03691) on enzymatic hydrolysis of pretreated corn stover by a *Trichoderma reesei* cellulase preparation.

The result of adding increasing amounts of the *Aspergillus aculeatus* P23NJS GH61 polypeptide (EXP03691) to the base cellulase mix are shown in FIG. 2. Addition of the *Aspergillus aculeatus* GH61 polypeptide provided a stimulation factor of 1.28 at a 100% addition level.

Figure 3:
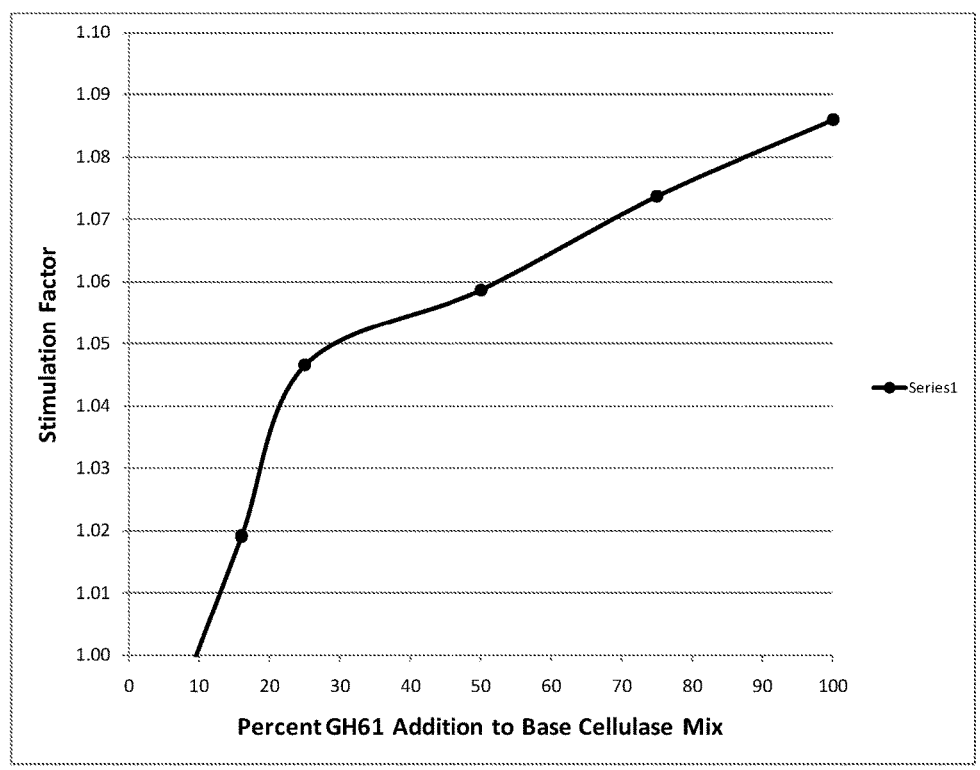
FIG. 3 shows the effect of an *Aspergillus aculeatus* P23NNN GH61 polypeptide (EXP03692) on enzymatic hydrolysis of pretreated corn stover by a *Trichoderma reesei* cellulase preparation.

The result of adding increasing amounts of the *Aspergillus aculeatus* P23NNN GH61 polypeptide (EXP03692) to the base cellulase mix are shown in FIG. 3. Addition of the *Aspergillus aculeatus* GH61 polypeptide provided a stimulation factor of 1.09 at a 100% addition level.

Figure 4:
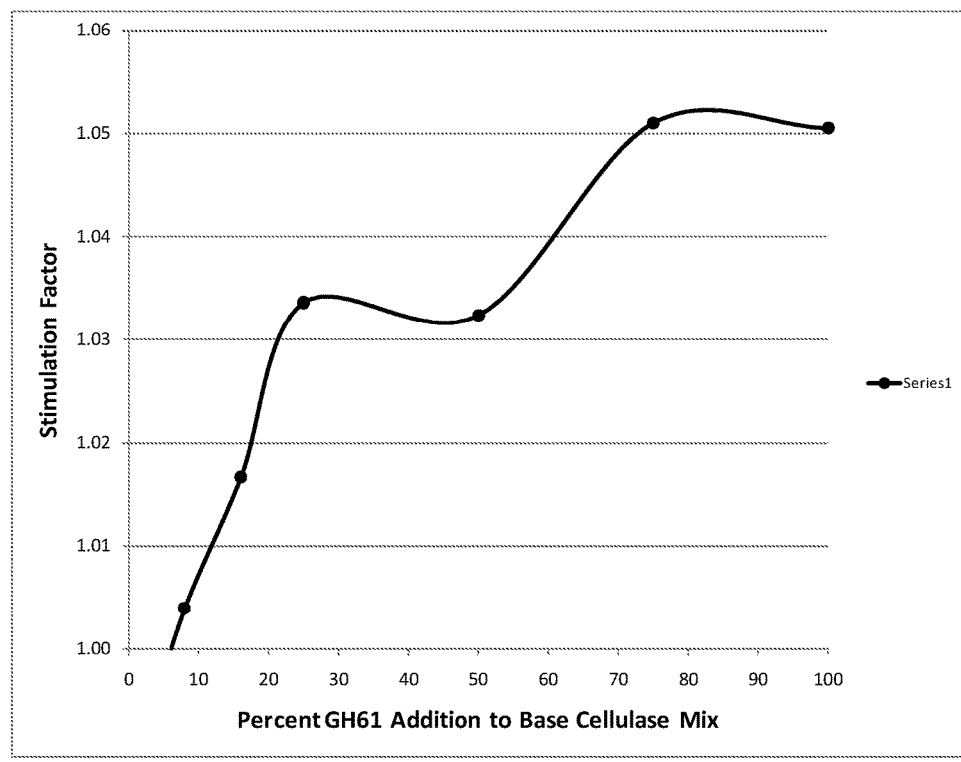
FIG. 4 shows the effect of an *Aspergillus aculeatus* P23NK1 GH61 polypeptide (EXP03693) on enzymatic hydrolysis of pretreated corn stover by a *Trichoderma reesei* cellulase preparation.

The result of adding increasing amounts of the *Aspergillus aculeatus* P23NK1 GH61 polypeptide (EXP03693) to the base cellulase mix are shown in FIG. 4. Addition of the *Aspergillus aculeatus* GH61 polypeptide provided a stimulation factor of 1.05 at a 100% addition level.

The present invention is further described by the following numbered paragraphs:

[1] An isolated polypeptide having cellulolytic enhancing activity, selected from the group consisting of: (a) a polypeptide having at least 60% sequence identity to the mature polypeptide of SEQ ID NO: 2, SEQ ID NO: 6, SEQ ID NO: 12, or SEQ ID NO: 14; at least 65% sequence identity to the mature polypeptide of SEQ ID NO: 8 or SEQ ID NO: 10, or at least 75% sequence identity to the mature polypeptide of SEQ ID NO: 4; (b) a polypeptide encoded by a polynucleotide that hybridizes under at least medium-high stringency conditions with (i) the mature polypeptide coding sequence of SEQ ID NO: 1 or the cDNA sequence thereof, SEQ ID NO: 3, SEQ ID NO: 5, SEQ ID NO: 7, SEQ ID NO: 9, SEQ ID NO: 11, or SEQ ID NO: 13 or the cDNA sequence thereof, or (ii) the full-length complement of (i); (c) a polypeptide encoded by a polynucleotide having at least 60% sequence identity to the mature polypeptide coding sequence of SEQ ID NO: 1 or the cDNA sequence thereof, SEQ ID NO: 5, SEQ ID NO: 11, or SEQ ID NO: 13, or the cDNA sequence thereof; at least 65% sequence identity to the mature polypeptide coding sequence of SEQ ID NO: 7 or SEQ ID NO: 9; or at least 75% sequence identity to the mature polypeptide coding sequence of SEQ ID NO: 3; (d) a variant of the mature polypeptide of SEQ ID NO: 2, SEQ ID NO: 4, SEQ ID NO: 6, SEQ ID NO: 8, SEQ ID NO: 10, SEQ ID NO: 12, or SEQ ID NO: 14 comprising a substitution, deletion, and/or insertion at one or more (e.g., several) positions; and (e) a fragment of the polypeptide of (a), (b), (c), or (d) that has cellulolytic enhancing activity.

[2] The polypeptide of paragraph 1, having a polypeptide having at least 60%, at least 65%, at least 70%, at least 75%, at least 80%, at least 81%, at least 83%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2, SEQ ID NO: 6, SEQ ID NO: 12, or SEQ ID NO: 14; at least 65%, at least 70%, at least 75%, at least 80%, at least 81%, at least 83%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 8 or SEQ ID NO: 10, or at least 75%, at least 80%, at least 81%, at least 83%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 4.

[3] The polypeptide of paragraph 1 or 2, which is encoded by a polynucleotide that hybridizes under medium-high, high, or very high stringency conditions with (i) the mature polypeptide coding sequence of SEQ ID NO: 1 or the cDNA sequence thereof, SEQ ID NO: 3, SEQ ID NO: 5, SEQ ID NO: 7, SEQ ID NO: 9, SEQ ID NO: 11, or SEQ ID NO: 13 or the cDNA sequence thereof, or (ii) the full-length complement of (i).

[4] The polypeptide of any of paragraphs 1-3, which is encoded by a polynucleotide having at least 60%, at least 65%, at least 70%, at least 75%, at least 80%, at least 81%, at least 83%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or the cDNA sequence thereof, SEQ ID NO: 5, SEQ ID NO: 11, or SEQ ID NO: 13 or the cDNA sequence thereof; at least 65%, at least 70%, at least 75%, at least 80%, at least 81%, at least 83%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 7 or SEQ ID NO: 9; or at least 75%, at least 80%, at least 81%, at least 83%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 3.

[5] The polypeptide of any of paragraphs 1-4, comprising or consisting of SEQ ID NO: 2, SEQ ID NO: 4, SEQ ID NO: 6, SEQ ID NO: 8, SEQ ID NO: 10, SEQ ID NO: 12, or SEQ ID NO: 14; or the mature polypeptide thereof.

[6] The polypeptide of paragraph 5, wherein the mature polypeptide is amino acids 21 to 344 of SEQ ID NO: 2, amino acids 26 to 400 of SEQ ID NO: 4, amino acids 21 to 389 of SEQ ID NO: 6, amino acids 22 to 405 of SEQ ID NO: 8, amino acids 20 to 427 of SEQ ID NO: 10, amino acids 18 to 267 of SEQ ID NO: 12, or amino acids 21 to 273 of SEQ ID NO: 14.

[7] The polypeptide of any of paragraphs 1-4, which is a variant of the mature polypeptide of SEQ ID NO: 2, SEQ ID NO: 4, SEQ ID NO: 6, SEQ ID NO: 8, SEQ ID NO: 10, SEQ ID NO: 12, or SEQ ID NO: 14 comprising a substitution, deletion, and/or insertion at one or more positions.

[8] The polypeptide of paragraph 1, which is a fragment of SEQ ID NO: 2, SEQ ID NO: 4, SEQ ID NO: 6, SEQ ID NO: 8, SEQ ID NO: 10, SEQ ID NO: 12, or SEQ ID NO: 14, wherein the fragment has cellulolytic enhancing activity.

[9] A composition comprising the polypeptide of any of paragraphs 1-8.

[10] An isolated polynucleotide encoding the polypeptide of any of paragraphs 1-8.

[11] A nucleic acid construct or expression vector comprising the polynucleotide of paragraph 10 operably linked to one or more control sequences that direct the production of the polypeptide in an expression host.

[12] A recombinant host cell comprising the polynucleotide of paragraph 10 operably linked to one or more control sequences that direct the production of the polypeptide.

[13] A method of producing the polypeptide of any of paragraphs 1-8, comprising: (a) cultivating a cell, which in its wild-type form produces the polypeptide, under conditions conducive for production of the polypeptide; and (b) recovering the polypeptide.

[14] A method of producing a polypeptide having cellulolytic enhancing activity, comprising: (a) cultivating the host cell of paragraph 12 under conditions conducive for production of the polypeptide; and (b) recovering the polypeptide.

[15] A transgenic plant, plant part or plant cell transformed with a polynucleotide encoding the polypeptide of any of paragraphs 1-8.

[16] A method of producing a polypeptide having cellulolytic enhancing activity, comprising: (a) cultivating the transgenic plant or plant cell of paragraph 15 under conditions conducive for production of the polypeptide; and (b) recovering the polypeptide.

[17] A method of producing a mutant of a parent cell, comprising inactivating a polynucleotide encoding the polypeptide of any of paragraphs 1-8, which results in the mutant producing less of the polypeptide than the parent cell.

[18] A mutant cell produced by the method of paragraph 17.

[19] The mutant cell of paragraph 18, further comprising a gene encoding a native or heterologous protein.

[20] A method of producing a protein, comprising: (a) cultivating the mutant cell of paragraph 18 or 19 under conditions conducive for production of the protein; and (b) recovering the protein.

[21] A double-stranded inhibitory RNA (dsRNA) molecule comprising a subsequence of the polynucleotide of paragraph 10, wherein optionally the dsRNA is an siRNA or an miRNA molecule.

[22] The double-stranded inhibitory RNA (dsRNA) molecule of paragraph 21, which is about 15, 16, 17, 18, 19, 20, 21, 22, 23, 24, 25 or more duplex nucleotides in length.

[23] A method of inhibiting the expression of a polypeptide having cellulolytic enhancing activity in a cell, comprising administering to the cell or expressing in the cell the double-stranded inhibitory RNA (dsRNA) molecule of paragraph 21 or 22.

[24] A cell produced by the method of paragraph 23.

[25] The cell of paragraph 24, further comprising a gene encoding a native or heterologous protein.

[26] A method of producing a protein, comprising: (a) cultivating the cell of paragraph 24 or 25 under conditions conducive for production of the protein; and (b) recovering the protein.

[27] An isolated polynucleotide encoding a signal peptide comprising or consisting of amino acids 1 to 20 of SEQ ID NO: 2, amino acids 1 to 25 of SEQ ID NO: 4, amino acids 1 to 20 of SEQ ID NO: 6, amino acids 1 to 21 of SEQ ID NO: 8, amino acids 1 to 19 of SEQ ID NO: 10, amino acids 1 to 17 of SEQ ID NO: 12, or amino acids 1 to 20 of SEQ ID NO: 14.

[28] A nucleic acid construct or expression vector comprising a gene encoding a protein operably linked to the polynucleotide of paragraph 27, wherein the gene is foreign to the polynucleotide encoding the signal peptide.

[29] A recombinant host cell comprising a gene encoding a protein operably linked to the polynucleotide of paragraph 27, wherein the gene is foreign to the polynucleotide encoding the signal peptide.

[30] A process of producing a protein, comprising: (a) cultivating a recombinant host cell comprising a gene encoding a protein operably linked to the polynucleotide of paragraph 27, wherein the gene is foreign to the polynucleotide encoding the signal peptide, under conditions conducive for production of the protein; and (b) recovering the protein.

[31] A whole broth formulation or cell culture composition comprising the polypeptide of any of paragraphs 1-8.

[32] A process for degrading or converting a cellulosic material, comprising: treating the cellulosic material with an enzyme composition in the presence of the polypeptide having cellulolytic enhancing activity of any of paragraphs 1-8.

[33] The process of paragraph 32, wherein the cellulosic material is pretreated.

[34] The process of paragraph 32 or 33, wherein the enzyme composition comprises one or more enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

[35] The process of paragraph 34, wherein the cellulase is one or more enzymes selected from the group consisting of an endoglucanase, a cellobiohydrolase, and a beta-glucosidase.

[36] The process of paragraph 34, wherein the hemicellulase is one or more enzymes selected from the group consisting of a xylanase, an acetylxylan esterase, a feruloyl esterase, an arabinofuranosidase, a xylosidase, and a glucuronidase.

[37] The process of any of paragraphs 32-36, further comprising recovering the degraded cellulosic material.

[38] The process of paragraph 37, wherein the degraded cellulosic material is a sugar.

[39] The process of paragraph 38, wherein the sugar is selected from the group consisting of glucose, xylose, mannose, galactose, and arabinose.

[40] A process for producing a fermentation product, comprising: (a) saccharifying a cellulosic material with an enzyme composition in the presence of the polypeptide having cellulolytic enhancing activity of any of paragraphs 1-8; (b) fermenting the saccharified cellulosic material with one or more fermenting microorganisms to produce the fermentation product; and (c) recovering the fermentation product from the fermentation.

[41] The process of paragraph 40, wherein the cellulosic material is pretreated.

[42] The process of paragraph 40 or 41, wherein the enzyme composition comprises one or more enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

[43] The process of paragraph 42, wherein the cellulase is one or more enzymes selected from the group consisting of an endoglucanase, a cellobiohydrolase, and a beta-glucosidase.

[44] The process of paragraph 42, wherein the hemicellulase is one or more enzymes selected from the group consisting of a xylanase, an acetylxylan esterase, a feruloyl esterase, an arabinofuranosidase, a xylosidase, and a glucuronidase.

[45] The process of any of paragraphs 40-44, wherein steps (a) and (b) are performed simultaneously in a simultaneous saccharification and fermentation.

[46] The process of any of paragraphs 40-45, wherein the fermentation product is an alcohol, an alkane, a cycloalkane, an alkene, an amino acid, a gas, isoprene, a ketone, an organic acid, or polyketide.

[47] A process of fermenting a cellulosic material, comprising: fermenting the cellulosic material with one or more fermenting microorganisms, wherein the cellulosic material is saccharified with an enzyme composition in the presence of a polypeptide having cellulolytic enhancing activity of any of paragraphs 1-8.

[48] The process of paragraph 47, wherein the fermenting of the cellulosic material produces a fermentation product.

[49] The process of paragraph 48, further comprising recovering the fermentation product from the fermentation.

[50] The process of any of paragraphs 47-49, wherein the cellulosic material is pretreated before saccharification.

[51] The process of any of paragraphs 47-50, wherein the enzyme composition comprises one or more enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

[52] The process of paragraph 51, wherein the cellulase is one or more enzymes selected from the group consisting of an endoglucanase, a cellobiohydrolase, and a beta-glucosidase.

[53] The process of paragraph 51, wherein the hemicellulase is one or more enzymes selected from the group consisting of a xylanase, an acetylxylan esterase, a feruloyl esterase, an arabinofuranosidase, a xylosidase, and a glucuronidase.

[54] The process of any of paragraphs 47-53, wherein the fermentation product is an alcohol, an alkane, a cycloalkane, an alkene, an amino acid, a gas, isoprene, a ketone, an organic acid, or polyketide.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A nucleic acid construct comprising a polynucleotide encoding a Family 61 glycoside hydrolase (GH61) polypeptide having cellulolytic enhancing activity, wherein the polynucleotide is operably linked to one or more heterologous control sequences that direct the production of the GH61 polypeptide and wherein the GH61 polypeptide is selected from the group consisting of:
   (a) a GH61 polypeptide having at least 90% sequence identity to the mature polypeptide of SEQ ID NO: 4, SEQ ID NO: 6, SEQ ID NO: 8, SEQ ID NO: 10, or SEQ ID NO: 14, or at least 95% sequence identity to the mature polypeptide of SEQ ID NO: 12;
   (b) a GH61 polypeptide encoded by a polynucleotide having at least 95% sequence identity to the mature polypeptide coding sequence of SEQ ID NO: 3, SEQ ID NO: 5, SEQ ID NO: 7, SEQ ID NO: 9, SEQ ID NO: 11, or SEQ ID NO: 13, or the cDNA sequence of SEQ ID NO: 5, SEQ ID NO: 11, or SEQ ID NO: 13;
   (c) a GH61 polypeptide comprising the mature polypeptide of SEQ ID NO: 4, SEQ ID NO: 6, SEQ ID NO: 8, SEQ ID NO: 10, SEQ ID NO: 12, or SEQ ID NO: 14; and
   (d) a GH61 polypeptide encoded by a polynucleotide comprising the mature polypeptide coding sequence of SEQ ID NO: 3, SEQ ID NO: 5, SEQ ID NO: 7, SEQ ID NO: 9, SEQ ID NO: 11, or SEQ ID NO: 13.

2. An isolated recombinant host cell transformed with the nucleic acid construct of claim 1.

3. A method of producing a GH61 polypeptide having cellulolytic enhancing activity, said method comprising:
   (a) cultivating the recombinant host cell of claim 2 under conditions conducive for production of the GH61 polypeptide; and
   (b) recovering the GH61 polypeptide.

4. A transgenic plant, plant part or plant cell transformed with the nucleic acid construct of claim 1 comprising a polynucleotide encoding the GH61 polypeptide having cellulolytic enhancing activity.

5. A method of producing a GH61 polypeptide having cellulolytic enhancing activity, said method comprising:
   (a) cultivating the transgenic plant or plant cell of claim 4 under conditions conducive for production of the GH61 polypeptide; and
   (b) recovering the GH61 polypeptide.

6. The nucleic acid construct of claim 1, wherein the GH61 polypeptide has at least 90% sequence identity to the mature polypeptide of SEQ ID NO: 4, SEQ ID NO: 6, SEQ ID NO: 8, SEQ ID NO: 10, or SEQ ID NO: 14.

7. The nucleic acid construct of claim 1, wherein the GH61 polypeptide has at least 91% sequence identity to the mature polypeptide of SEQ ID NO: 4, SEQ ID NO: 6, SEQ ID NO: 8, SEQ ID NO: 10, or SEQ ID NO: 14.

8. The nucleic acid construct of claim 1, wherein the GH61 polypeptide has at least 92% sequence identity to the mature polypeptide of SEQ ID NO: 4, SEQ ID NO: 6, SEQ ID NO: 8, SEQ ID NO: 10, or SEQ ID NO: 14.

9. The nucleic acid construct of claim 1, wherein the GH61 polypeptide has at least 93% sequence identity to the mature polypeptide of SEQ ID NO: 4, SEQ ID NO: 6, SEQ ID NO: 8, SEQ ID NO: 10, or SEQ ID NO: 14.

10. The nucleic acid construct of claim 1, wherein the GH61 polypeptide has at least 94% sequence identity to the mature polypeptide of SEQ ID NO: 4, SEQ ID NO: 6, SEQ ID NO: 8, SEQ ID NO: 10, or SEQ ID NO: 14.

11. The nucleic acid construct of claim 1, wherein the GH61 polypeptide has at least 95% sequence identity to the mature polypeptide of SEQ ID NO: 4, SEQ ID NO: 6, SEQ ID NO: 8, SEQ ID NO: 10, SEQ ID NO: 12, or SEQ ID NO: 14.

12. The nucleic acid construct of claim 1, wherein the GH61 polypeptide has at least 96% sequence identity to the mature polypeptide of SEQ ID NO: 4, SEQ ID NO: 6, SEQ ID NO: 8, SEQ ID NO: 10, SEQ ID NO: 12, or SEQ ID NO: 14.

13. The nucleic acid construct of claim 1, wherein the GH61 polypeptide has at least 97% sequence identity to the mature polypeptide of SEQ ID NO: 4, SEQ ID NO: 6, SEQ ID NO: 8, SEQ ID NO: 10, SEQ ID NO: 12, or SEQ ID NO: 14.

14. The nucleic acid construct of claim 1, wherein the GH61 polypeptide has at least 98% sequence identity to the mature polypeptide of SEQ ID NO: 4, SEQ ID NO: 6, SEQ ID NO: 8, SEQ ID NO: 10, SEQ ID NO: 12, or SEQ ID NO: 14.

15. The nucleic acid construct of claim 1, wherein the GH61 polypeptide has at least 99% sequence identity to the mature polypeptide of SEQ ID NO: 4, SEQ ID NO: 6, SEQ ID NO: 8, SEQ ID NO: 10, SEQ ID NO: 12, or SEQ ID NO: 14.

16. The nucleic acid construct of claim 1, wherein the GH61 polypeptide comprises the mature polypeptide of SEQ ID NO: 4.

17. The nucleic acid construct of claim 1, wherein the GH61 polypeptide is encoded by a polynucleotide comprising the mature polypeptide coding sequence of SEQ ID NO: 3, SEQ ID NO: 5, SEQ ID NO: 7, SEQ ID NO: 9, SEQ ID NO: 11, or SEQ ID NO: 13.

18. The nucleic acid construct of claim 1, wherein the GH61 polypeptide comprises the mature polypeptide of SEQ ID NO: 6.

19. The nucleic acid construct of claim 1, wherein the GH61 polypeptide comprises the mature polypeptide of SEQ ID NO: 8.

20. The nucleic acid construct of claim 1, wherein the GH61 polypeptide comprises the mature polypeptide of SEQ ID NO: 10.

21. The nucleic acid construct of claim 1, wherein the GH61 polypeptide comprises the mature polypeptide of SEQ ID NO: 12.

22. The nucleic acid construct of claim 1, wherein the GH61 polypeptide comprises the mature polypeptide of SEQ ID NO: 14.

* * * * *